US010335501B2

(12) United States Patent
Bradbury et al.

(10) Patent No.: US 10,335,501 B2
(45) Date of Patent: Jul. 2, 2019

(54) CYCLIC PEPTIDES WITH ENHANCED NERVE-BINDING SELECTIVELY, NANOPARTICLES BOUND WITH SAID CYCLIC PEPTIDES, AND USE OF SAME FOR REAL-TIME IN VIVO NERVE TISSUE IMAGING

(71) Applicants: Memorial Sloan Kettering Cancer Center, New York, NY (US); Cornell University, Ithaca, NY (US)

(72) Inventors: Michelle S. Bradbury, New York, NY (US); Barney Yoo, New York, NY (US); Ulrich Wiesner, Ithaca, NY (US); Peiming Chen, New York, NY (US); Kai Ma, Ithaca, NY (US); Snehal G. Patel, New York, NY (US); Daniella Karassawa Zanoni, New York, NY (US)

(73) Assignees: Memorial Sloan Kettering Cancer Center, New York, NY (US); Cornell University, Ithaca, NY (US)

( * ) Notice: Subject to any disclaimer, the term of this patent is extended or adjusted under 35 U.S.C. 154(b) by 145 days.

(21) Appl. No.: 14/969,877

(22) Filed: Dec. 15, 2015

(65) Prior Publication Data

US 2016/0166714 A1 Jun. 16, 2016

Related U.S. Application Data

(60) Provisional application No. 62/092,191, filed on Dec. 15, 2014.

(51) Int. Cl.
*A61B 5/00* (2006.01)
*A61K 9/00* (2006.01)
*A61K 49/00* (2006.01)

(52) U.S. Cl.
CPC ........ *A61K 49/0056* (2013.01); *A61B 5/0071* (2013.01); *A61B 5/4893* (2013.01); *A61K 9/0014* (2013.01); *A61K 9/0019* (2013.01); *A61K 49/0032* (2013.01); *A61K 49/0065* (2013.01); *A61K 49/0093* (2013.01)

(58) Field of Classification Search
None
See application file for complete search history.

(56) References Cited

U.S. PATENT DOCUMENTS

| | | |
|---|---|---|
| 4,981,977 A | 1/1991 | Southwick et al. |
| 5,268,486 A | 12/1993 | Waggoner et al. |
| 5,486,616 A | 1/1996 | Waggoner et al. |
| 5,569,587 A | 10/1996 | Waggoner |
| 5,569,766 A | 10/1996 | Waggoner et al. |
| 5,627,027 A | 5/1997 | Waggoner |
| 5,808,044 A | 9/1998 | Brush et al. |
| 5,877,310 A | 3/1999 | Reddington et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,133,445 A | 10/2000 | Waggoner et al. |
| 6,136,612 A | 10/2000 | Della Ciana et al. |
| 6,448,008 B1 | 9/2002 | Caputo et al. |
| 6,534,041 B1 | 3/2003 | Licha et al. |
| 6,747,159 B2 | 6/2004 | Caputo et al. |
| 7,445,767 B2 | 11/2008 | Licha et al. |
| 7,473,415 B2 | 1/2009 | Kawakami et al. |
| 7,488,468 B1 | 2/2009 | Miwa et al. |
| 7,547,721 B1 | 6/2009 | Miwa et al. |
| 8,298,677 B2 | 10/2012 | Wiesner et al. |
| 8,409,876 B2 | 4/2013 | Wiesner et al. |
| 2012/0148499 A1* | 6/2012 | Tsien ................. A61K 49/0032 424/9.6 |
| 2013/0039848 A1 | 2/2013 | Bradbury et al. |
| 2015/0182118 A1 | 7/2015 | Bradbury et al. |
| 2015/0343091 A1 | 12/2015 | Yoo et al. |

FOREIGN PATENT DOCUMENTS

| | | |
|---|---|---|
| EP | 1065250 A1 | 1/2001 |
| EP | 1113822 A1 | 7/2001 |
| EP | 1237583 A1 | 9/2002 |
| EP | 0796111 B1 | 4/2003 |
| EP | 1181940 B1 | 12/2004 |
| EP | 1480683 A2 | 12/2004 |
| EP | 1679082 A1 | 7/2006 |
| EP | 0988060 B1 | 6/2007 |
| EP | 1833513 A1 | 9/2007 |
| WO | WO-96/17628 A1 | 6/1996 |
| WO | WO-97/40104 A1 | 10/1997 |

(Continued)

OTHER PUBLICATIONS

Horswill et al. ("Cyclic Peptides, a Chemical Genetics Tool for Biologist" Cell Cycle, 552-555: 2005).*
Bradbury, M.S. et al., Clinically-translated silica nanoparticles as dual-modality cancer-targeted probes for image-guided surgery and interventions, Integr. Biol., 5:74-86 (2013).
Burns, A. et al., U. Fluorescent core-shell silica nanoparticles: towards "Lab on a Particle" architectures for nanobiotechnology. Chem Soc Rev., 35(11):1028-42 (2006).
Herz, E. et al., Dye structure-optical property correlations in near-infrared fluorescent core-shell silica nanoparticles, J. Mater. Chem., 19:6341-6347 (2009).

(Continued)

*Primary Examiner* — James H Alstrum-Acevedo
*Assistant Examiner* — Tara L Martinez
(74) *Attorney, Agent, or Firm* — Choate, Hall & Stewart LLP; William R. Haulbrook; Margo R. Monroe

(57) ABSTRACT

Described herein are cyclic peptides, nanoparticles bound with cyclic peptides, and methods for using said cyclic peptides and/or said nanoparticles bound with cyclic peptides for intraoperative nerve tissue imaging.

6 Claims, 23 Drawing Sheets

Specification includes a Sequence Listing.

(56) References Cited

FOREIGN PATENT DOCUMENTS

| WO | WO-98/47538 A2 | 10/1998 |
| --- | --- | --- |
| WO | WO-99/51702 A1 | 10/1999 |
| WO | WO-00/16810 A1 | 3/2000 |
| WO | WO-01/21624 A1 | 3/2001 |
| WO | WO-01/43781 A1 | 6/2001 |
| WO | WO-03/074091 A2 | 9/2003 |
| WO | WO-06/072580 A1 | 7/2006 |
| WO | WO-2006/105392 A2 | 10/2006 |
| WO | WO-2010/121023 A2 | 10/2010 |
| WO | WO-2011/003109 A1 | 1/2011 |
| WO | WO-2012/031250 A2 | 3/2012 |
| WO | WO 2014/093251 * | 6/2014 |
| WO | WO-2014/145606 A1 | 9/2014 |
| WO | WO-2016/100340 A1 | 6/2016 |
| WO | WO-2017/106525 A1 | 6/2017 |

OTHER PUBLICATIONS

Ozmen, B. and Akkaya, E. U., Infrared fluorescence sensing of submicromolar calcium: pushing the limits of photoinduced electron transfer, Tetrahedron Letters, 41:9185-88 (2000).

Phillips, E. et al., Clinical Translation of an Ultrasmall Inorganic Optical-PET Imaging Nanoparticle Probe, Science Translational Medicine, 6(260):1 (2014).

Whitney, M. A. et al., Fluorescent peptides highlight peripheral nerves during surgery in mice, Nature Biotechnology, 29(4):352 (2011).

Detappe, A. et al., Advanced multimodal nanoparticles delay tumor progression with clinical radiation therapy, Journal of Controlled Release, 238:103-113 (2016).

Hama, Y. et al., Simultaneous two-color spectral fluorescence lymphangiography with near infrared quantum dots to map two lymphatic flows from the breast and the upper extremity, Breast Cancer Research and Treatment, 103:23-28 (2007).

Hama, Y. et al., Two-Color Lymphatic Mapping Using Ig-Conjugated Near Infrared Optical Probes, Journal of Investigative Dermatology, 127:2351-2356 (2007).

International Partial Search Report, PCT/US2016/066969, 3 pages, dated Apr. 4, 2017.

International Search Report, PCT/US2016/066969, 7 pages, dated May 26, 2017.

Written Opinion, PCT/US2016/066969, 10 pages, dated May 26, 2017.

* cited by examiner

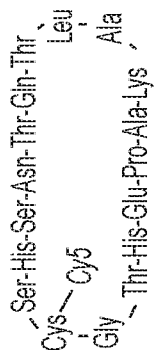
LINEAR PEPTIDE-Cy5
Ac-Ser-His-Ser-Asn-Thr-Gln-Thr
                              \
                               Leu
Cy5                             \
 |                               Ala
Cys-Gly-Thr-His-Glu-Pro-Ala-Lys´
FIG. 1A
CYCLIC PEPTIDE-Cy5
 ,Ser-His-Ser-Asn-Thr-Gln-Thr
,                             \
                               Leu
Cys—Cy5                         \
 Gly                             Ala
   `Thr-His-Glu-Pro-Ala-Lys´
FIG. 1B
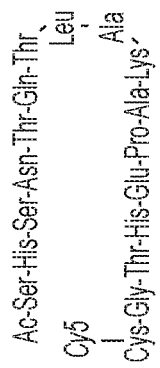
LCMS-LINEAR PEPTIDE-Cy5
MS DATA
            CALC    OBS.
[M+2H]²⁺   1301.6  1202.1
[M+3H]³⁺    853.0   858.4
FIG. 1C
LCMS-CYCLIC PEPTIDE-Cy5
MS DATA
            CALC    OBS.
[M+2H]²⁺   1271.5  1271.6
[M+3H]³⁺    848.0   848.4
FIG. 1D

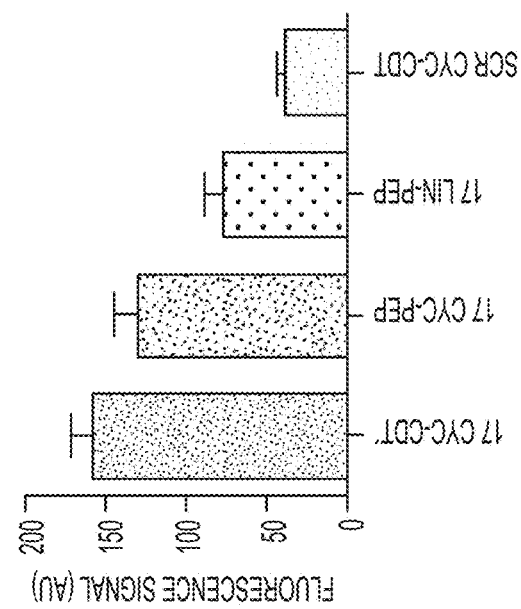
FIG. 10E
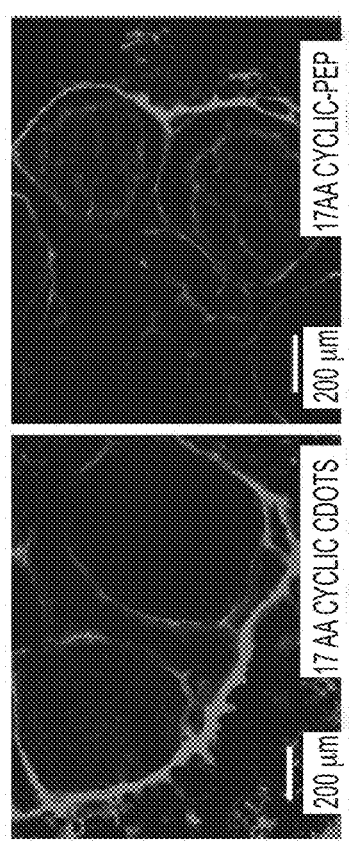
FIG. 10A
FIG. 10C
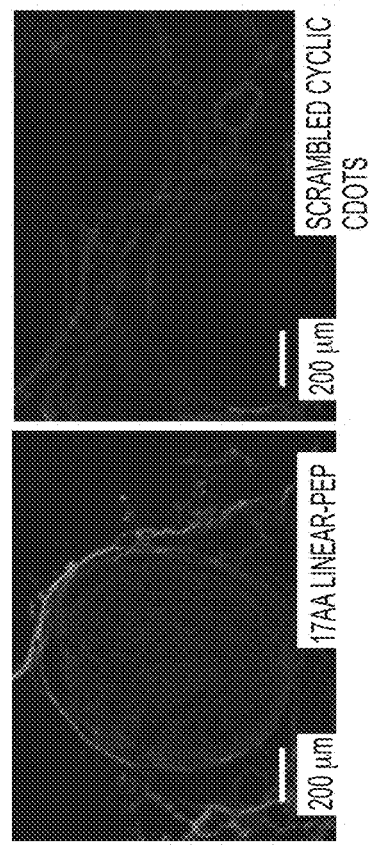
FIG. 10B
FIG. 10D

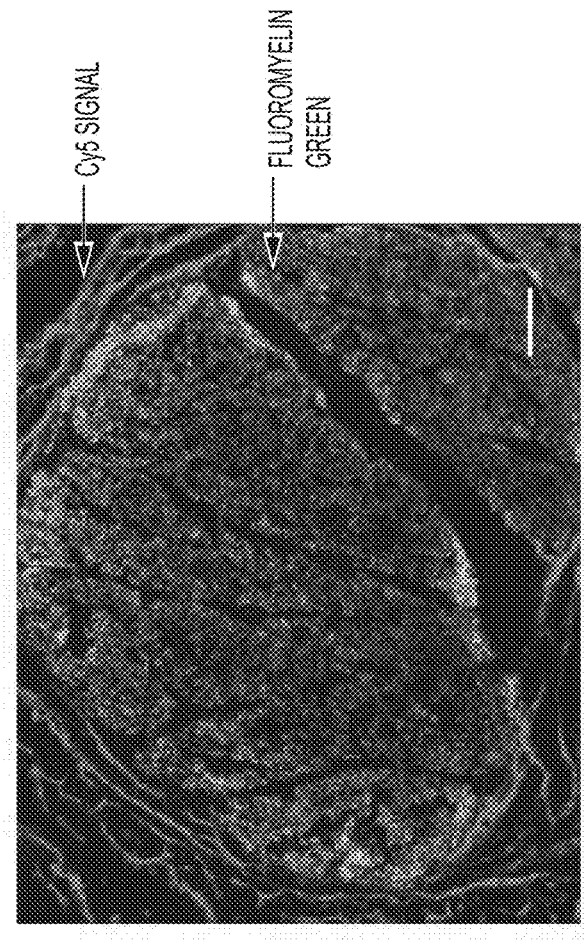
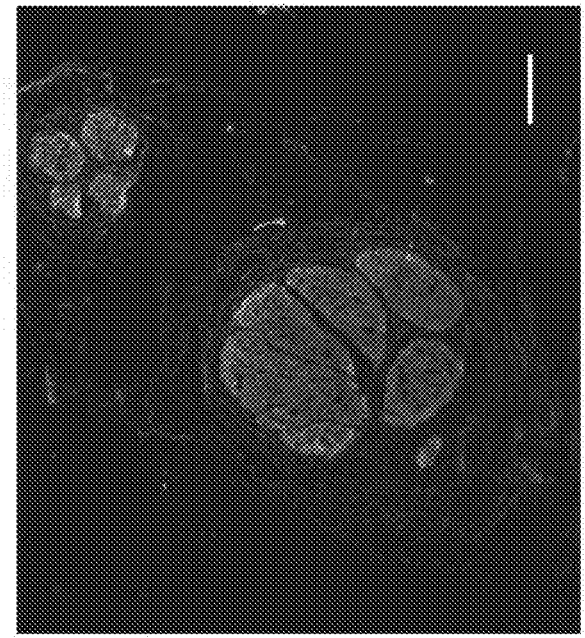
FIG. 11A
FIG. 11B

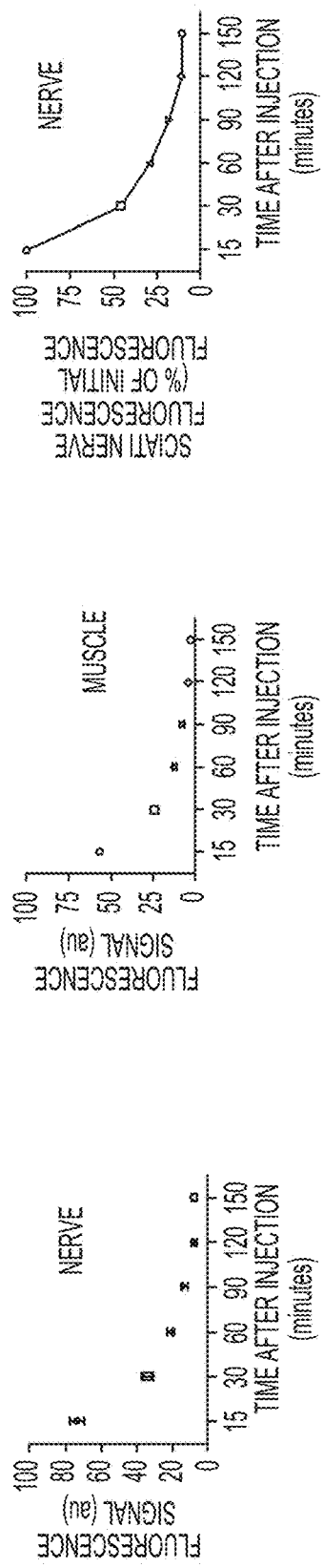
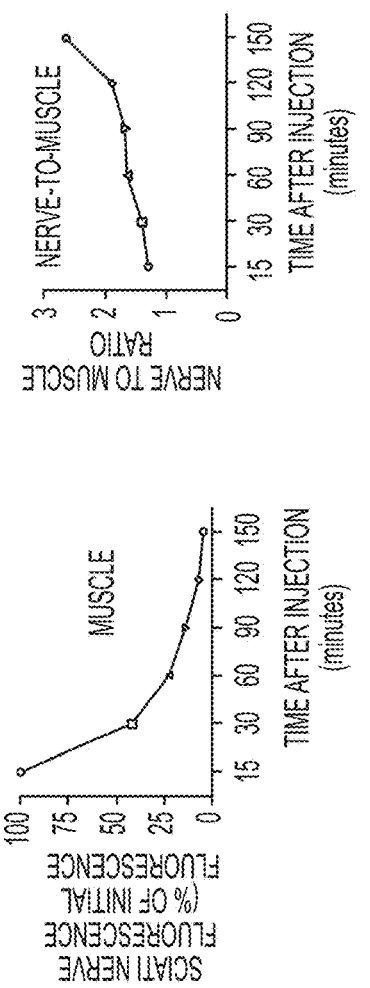

SEQUENCE LISTING

```
<160> NUMBER OF SEQ ID NOS: 17

<210> SEQ ID NO 1
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Cyclic peptide"

<400> SEQUENCE: 1

Asn Thr Gln Thr Leu Ala Lys Ala Pro Glu His Thr
1               5                   10
```

<210> SEQ ID NO 2
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Cyclic peptide"

<400> SEQUENCE: 2

Thr Tyr Thr Asp Trp Leu Asn Phe Trp Ala Trp Pro
1               5                   10

<210> SEQ ID NO 3
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Cyclic peptide"

<400> SEQUENCE: 3

Lys Ser Leu Ser Arg His Asp His Ile His His His
1               5                   10

<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Cyclic peptide"

<400> SEQUENCE: 4

Asp Phe Thr Lys Thr Ser Pro Leu Gly Ile His
1               5                   10

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Ser His Ser Ser Thr Ala Arg Asp Leu Trp Pro His Gly Lys Glu Gly
1               5                   10                  15

Cys

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"

<400> SEQUENCE: 6

Asn Thr Gln Thr Leu Ala Lys Ala Pro Glu His Thr
1               5                   10

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ser His Ser Asn Thr Gln Thr Leu Ala Lys Ala Pro Glu His Thr Gly
1               5                   10                  15

Cys

<210> SEQ ID NO 8
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Thr Tyr Thr Asp Trp Leu Asn Phe Trp Ala Trp Pro
1               5                   10

<210> SEQ ID NO 9
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Lys Ser Leu Ser Arg His Asp His Ile His His His
1               5                   10

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Asp Phe Thr Lys Thr Ser Pro Leu Gly Ile His
1               5                   10

<210> SEQ ID NO 11
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:

```
<221> NAME/KEY: source
<223> OTHER INFORMATION: /note="Cyclic peptide"

<400> SEQUENCE: 11

Ser His Ser Asn Thr Gln Thr Leu Ala Lys Ala Pro Glu His Thr Gly
1               5                   10                  15
Cys

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Thr Leu Ala Lys Ala Pro Glu His Thr Cys
1               5                   10

<210> SEQ ID NO 13
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Cyclic peptide"

<400> SEQUENCE: 13

Thr Leu Ala Lys Ala Pro Glu His Thr Cys
1               5                   10

<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Cyclic peptide"

<400> SEQUENCE: 14

Asn Thr Gln Thr Leu Lys Lys Ala Pro Glu His Thr Gly Cys
1               5                   10

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser His Ser Ser Thr Ala Arg Asp Leu Trp Pro His Gly Ser Glu Gly
1               5                   10                  15
Cys
```

```
<210> SEQ ID NO 16
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Cyclic peptide"

<400> SEQUENCE: 16

Ser His Ser Ser Thr Ala Arg Asp Leu Trp Pro His Gly Ser Glu Gly
1               5                   10                  15

Cys

<210> SEQ ID NO 17
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Cyclic peptide"

<400> SEQUENCE: 17

Arg Gly Asp Tyr
1
```

CYCLIC PEPTIDES WITH ENHANCED NERVE-BINDING SELECTIVELY, NANOPARTICLES BOUND WITH SAID CYCLIC PEPTIDES, AND USE OF SAME FOR REAL-TIME IN VIVO NERVE TISSUE IMAGING

CROSS-REFERENCE TO RELATED APPLICATIONS

This application claims the benefit of U.S. Provisional Application No. 62/092,191, filed on Dec. 15, 2014, the text of which is hereby incorporated by reference herein in its entirety.

GOVERNMENT SUPPORT

This invention was made with government support under CA199081 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 22, 2016, is named 2016-02-29_SL.txt and is 5,728 bytes in size.

FIELD OF THE INVENTION

This invention relates generally to cyclic peptides, nanoparticles bound with cyclic peptides, and methods for using said cyclic peptides and/or said nanoparticles bound with cyclic peptides for intraoperative nerve tissue imaging.

BACKGROUND

Many surgical procedures carry the risk of accidental nerve damage or transection, which can result in significant problems such as chronic pain or paralysis. There has been research in the use of near-infrared (NIR) agents to highlight nerve tissue during surgery, thereby enhancing the surgeon's ability to avoid cutting or damaging the highlighted nerve tissue. For example, molecules such as distyrylbenzene and oxazine derivatives have been used, but they lack the necessary binding characteristics and/or spectral properties needed to be effective for intraoperative use in humans and other mammals.

Whitney et al. identified several nerve binding polypeptides by applying phage display methodologies against excised murine peripheral nerves (Whitney, M. A.; Crisp, J. L.; Nguyen, L. T.; Friedman, B.; Gross, L. A.; Steinbach, P.; Tsien, R. Y.; Nguyen, Q. T. *Nat. Biotech.* 2011, 29, 352). The sequences were subsequently labeled with a fluorophore or NIR dye, and evaluated in vitro and in vivo for binding. The sequence that provided the highest contrast over background was a 17-residue polypeptide, NP41 (FIG. 1A). There is a need for nerve-binding agents with enhanced selectivity for nerve tissue and for improved spectral properties for intraoperative use.

SUMMARY

Described herein are cyclic peptides, nanoparticles bound with cyclic peptides, and methods for using said cyclic peptides and/or said nanoparticles bound with cyclic peptides for intraoperative nerve tissue imaging.

In one aspect, the invention is directed to a nerve-binding peptide conjugate comprising: a cyclic peptide; a nanoparticle; a fluorescent agent; and a linker moiety. In another aspect, the invention is directed to a nerve-binding peptide conjugate comprising: a linear polypeptide; a nanoparticle; a fluorescent agent; and a linker moiety.

In certain embodiments (of either aspect), the nanoparticle comprises: a silica-based core; the fluorescent agent within the core; a silica shell surrounding at least a portion of the core; the linker moiety attached to the nanoparticle; and optionally, from one to twenty peptide ligands attached to the polymer-coated nanoparticle.

In certain embodiments (of either aspect), the nanoparticle is an ultrasmall particle (e.g., with an average diameter less than 100 nm, e,g., less than 50 nm, e.g., less than 30 nm, e.g., less than 20 nm, e.g., less than 10 nm) (e.g., wherein the ultrasmall nanoparticle is a C dot or C' dot).

In certain embodiments (of either aspect), the linker moiety comprises one or more members selected from the group consisting of polyethylene glycol (PEG), $PEG_2$, and para-aminobenzyloxy carbamate (PABC) (e.g., wherein the linker moiety has from 2 to 50 atoms). In certain embodiments, the linker moiety comprises one or more of the linker moieties described in U.S. patent application Ser. No. 14/722,307, filed May 27, 2015, published as U.S. Patent Application Publication No. US 2015/0343091, the text of which is incorporated herein by reference in its entirety.

In certain embodiments, the cyclic peptide is bound to the nanoparticle via the linker moiety. In certain embodiments (of either aspect), the fluorescent agent comprises a cyanine dye, e.g., Cy5 or Cy5.5. In certain embodiments (of either aspect), the nerve-binding peptide conjugate has from 5 to 20 amino acid residues and/or a 15 atom to 60 atom macrocycle. In certain embodiments (of either aspect), the nerve-binding peptide conjugate has 17 amino acid residues and/or a 51 atom macrocycle.

In certain embodiments, the cyclic peptide comprises the peptide sequence NTQTLAKAPEHT (SEQ ID NO: 1). In certain embodiments, the macrocycle is formed by cyclizing the peptide head-to-tail, or by introducing a covalent bond internal to the sequence. In certain embodiments, the cyclic peptide comprises a peptide sequence selected from the group consisting of TYTDWLNFWAWP (SEQ ID NO: 2), KSLSRHDHIHHH (SEQ ID NO: 3), and DFTKTSPLGIH (SEQ ID NO: 4).

In another aspect, the invention is directed to a cyclic peptide comprising the peptide sequence NTQTLAKAPEHT (SEQ ID NO: 1).

In another aspect, the invention is directed to a cyclic peptide comprising a peptide sequence selected from the group consisting of TYTDWLNFWAWP (SEQ ID NO: 2), KSLSRHDHIHHH (SEQ ID NO: 3), and DFTKTSPLGIH (SEQ ID NO: 4).

In another aspect, the invention is directed to a cyclic peptide composition comprising: a fluorescent agent; and a cyclic peptide comprising the peptide sequence NTQTLAKAPEHT (SEQ ID NO: 1).

In another aspect, the invention is directed to a cyclic peptide composition comprising: a fluorescent agent; and a cyclic peptide comprising a peptide sequence selected from the group consisting of TYTDWLNFWAWP (SEQ ID NO: 2), KSLSRHDHIHHH (SEQ ID NO: 3), and DFTKTSPLGIH (SEQ ID NO: 4).

In certain embodiments, the cyclic peptide comprises a macrocycle. In certain embodiments, the macrocycle is formed by cyclizing the peptide head-to-tail, or by introducing a covalent bond internal to the sequence.

In another aspect, the invention is directed to a cyclic peptide composition comprising a cyclic peptide having a structure as shown in FIG. 1B or FIGS. 4A-4H. In certain embodiments, the cyclic peptide is attached to a nanoparticle. In certain embodiments, the cyclic peptide is attached covalently or non-covalently to the nanoparticle via a linker moiety. In certain embodiments, the cyclic peptide is functionalized.

In certain embodiments of any of the above aspects, the composition additionally comprises a radiolabel.

In another aspect, the invention is directed to an imaging method comprising: administering to a subject a formulation comprising the composition of any one of the above aspects and allowing the composition to selectively bind to nerve tissue of the subject; exposing tissue of the subject to excitation light; and detecting light emitted by the fluorescent agent of the composition to create an image and displaying the image.

In certain embodiments, light emitted from the nerve tissue is more intense than light emitted from surrounding tissue (e.g., the nerve-to-muscle signal ratio is at least 2) such that the nerve tissue is visually distinguishable from the surrounding tissue. In certain embodiments, light emitted from the nerve tissue is detectable at least as early as 15 minutes following administration of the formulation to the subject (e.g., wherein the subject is an animal, e.g., wherein the subject is a human). In certain embodiments, light emitted from the nerve tissue is detectable at least as long as 1 hour (e.g., at least 1 hour, at least 2 hours, at least 3 hours, or at least 4 hours) following administration of the formulation to the subject (e.g., wherein the subject is an animal, e.g., wherein the subject is a human).

In certain embodiments, administering comprises topically applying the formulation to a peripheral nerve trunk adjacent to or within the vicinity of a metastatic lymph node or primary tumor after surgical exposure. In certain embodiments, the method comprises topically applying the formulation to a peripheral nerve trunk (e.g., adjacent to or within the vicinity of a metastatic lymph node or primary tumor after surgical exposure), allowing the composition of the formulation to diffuse from the nerve trunk to smaller branches of the nerve tissue, and detecting light emitted by the fluorescent agent of the composition to create an image of the smaller branches of the nerve tissue.

In certain embodiments, the formulation is administered intravenously (by I.V.). In certain embodiments, the formulation is locally administered. In certain embodiments, exposing the tissue of the subject to excitation light occurs during a surgical procedure. In certain embodiments, the image is a video and/or still image and/or real-time video. In certain embodiments, the image is displayed to a surgeon during a surgical procedure conducted on the subject.

In another aspect, the invention is directed to an imaging method comprising: exposing tissue of a subject to excitation light, a formulation comprising the composition of any one of the above aspects having been administered to the subject; and detecting light emitted by the fluorescent agent of the composition.

In certain embodiments, the detecting step comprises detecting light emitted by the fluorescent agent of the composition to create an image and displaying the image. In certain embodiments, the method further comprises the step of administering the composition to the subject.

In certain embodiments, light emitted from the nerve tissue is more intense than light emitted from surrounding tissue (e.g., the nerve-to-muscle signal ratio is at least 2) such that the nerve tissue is visually distinguishable from the surrounding tissue. In certain embodiments, light emitted from the nerve tissue is detectable at least as early as 15 minutes following administration of the formulation to the subject (e.g., wherein the subject is an animal, e.g., wherein the subject is a human). In certain embodiments, light emitted from the nerve tissue is detectable at least as long as 1 hour (e.g., at least 1 hour, at least 2 hours, at least 3 hours, or at least 4 hours) following administration of the formulation to the subject (e.g., wherein the subject is an animal, e.g., wherein the subject is a human). In certain embodiments, the formulation has been administered by topical application to a peripheral nerve trunk adjacent to or within the vicinity of a metastatic lymph node or primary tumor after surgical exposure. In certain embodiments, the formulation has been administered by topical application to a peripheral nerve trunk (e.g., adjacent to or within the vicinity of a metastatic lymph node or primary tumor after surgical exposure) such that the composition of the formulation has diffused from the nerve trunk to smaller branches of the nerve tissue, wherein the method comprises detecting light emitted by the fluorescent agent of the composition to create an image of the smaller branches of the nerve tissue. In certain embodiments, the formulation is administered intravenously (by I.V.). In certain embodiments, the formulation is locally administered.

In certain embodiments, exposing the tissue of the subject to excitation light occurs during a surgical procedure. In certain embodiments, the detecting step comprises detecting light emitted by the fluorescent agent of the composition to create an image and displaying the image, wherein the image is a video and/or still image and/or real-time video. In certain embodiments, the image is displayed to a surgeon during a surgical procedure conducted on the subject.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance or formulation into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous. In certain embodiments, the substance or formulation is administered via local injection vs. IV administration. For example, substances or formulations with peptide-containing compositions (e.g., both particle-containing and non-particle-containing compositions) can be locally injected in a sufficiently high concentration for imaging purposes. In certain embodiments, non-particle peptide-containing compositions are administered via IV.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Detector": As used herein, "detector" refers to any detector of electromagnetic radiation including, but not limited to, CCD camera, photomultiplier tubes, photodiodes, and avalanche photodiodes.

"Image": As used herein, the term "image" is understood to mean a visual display or any data representation that may be interpreted for visual display. For example, a three-dimensional image may include a dataset of values of a given quantity that varies in three spatial dimensions. A three-dimensional image (e.g., a three-dimensional data representation) may be displayed in two-dimensions (e.g., on a two-dimensional screen, or on a two-dimensional printout). The term "image" may refer, for example, to an optical image, an x-ray image, an image generated by: positron emission tomography (PET), magnetic resonance, (MR) single photon emission computed tomography (SPECT), and/or ultrasound, and any combination of these.

"Peptide" or "Polypeptide": The term "peptide" or "polypeptide" refers to a string of at least two (e.g., at least three) amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/dadgrp/Unnatstruct.gif, which displays structures of non-natural amino acids that have been successfully incorporated into functional ion channels) and/or amino acid analogs as are known in the art may alternatively be employed). In some embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Radiolabel": As used herein, "radiolabel" refers to a moiety comprising a radioactive isotope of at least one element. Exemplary suitable radiolabels include but are not limited to those described herein. In some embodiments, a radiolabel is one used in positron emission tomography (PET). In some embodiments, a radiolabel is one used in single-photon emission computed tomography (SPECT). In some embodiments, radioisotopes comprise $^{99m}$Tc, $^{111}$In, $^{64}$Cu, $^{67}$Ga, $^{186}$Re, $^{188}$Re, $^{153}$Sm, $^{177}$Lu, $^{67}$Cu, $^{123}$I, $^{124}$I, $^{125}$I, $^{11}$C, $^{3}$N, $^{15}$O, $^{18}$F, $^{186}$Re, $^{188}$Re, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{67}$Cu, $^{105}$Rh, $^{111}$Ag, $^{89}$Zr, $^{225}$Ac, and $^{192}$Ir.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIGS. 1A-1D show examples of nerve binding peptide-Cy5 conjugates.

FIG. 1A shows a linear nerve binding peptide with Cy5 (Ac=acetyl group at N-terminus) (SEQ ID NO: 6).

FIG. 1B shows a cyclic nerve binding peptide with Cy5 (SEQ ID NO: 11).

FIG. 1C shows liquid chromatography mass spectrometry (LCMS) of linear peptide.

FIG. 1D shows LCMS of cyclic peptide. For LCMS, samples were run on a Waters, 4.6×50 mm C18 column, 5-95% acetonitrile in water (0.1% TFA) in 10 min. Mass spectrometry data confirming product is in black boxes.

FIG. 4A discloses SEQ ID NO: 12, FIG. 4B discloses SEQ ID NO: 13, FIG. 4C discloses SEQ ID NO: 13, FIG. 4D discloses SEQ ID NO: 14, FIG. 4E discloses SEQ ID NO: 7, FIG. 4F discloses SEQ ID NO: 14, FIG. 4G discloses SEQ ID NO: 15 and FIG. 4H discloses SEQ ID NO: 16.

FIGS. 10A-10E show cross-sectional fluorescence microscopy of human sciatic nerve specimens post-incubation with peptide-dye conjugates or fluorescent nerve binding peptide (NBP)-functionalized particle-based probes (e.g., Cy5-NBP-C dots).

FIGS. 11A and 11B show localization of 17 AA residue cyclic peptide-dye conjugates in human sciatic nerve specimens.

FIGS. 16A-16E show in vivo imaging of sciatic nerve and muscle fluorescence signal vs. time post-injection of 150 nmoles of 17 AA cyclic nerve binding peptides.

DETAILED DESCRIPTION

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

In the experiments described herein, linear polypeptides were cyclized, leading to a more rigid structure and enhancement in binding affinities and selectivities. For the studies presented, optimized conditions and high product yields were achieved using dimethylformamide (DMF) as the solvent and (benzotriazol-1-yloxy) tripyrrolidinophosphonium hexafluorophosphate (PyBOP) as the coupling agent.

Figure 2:
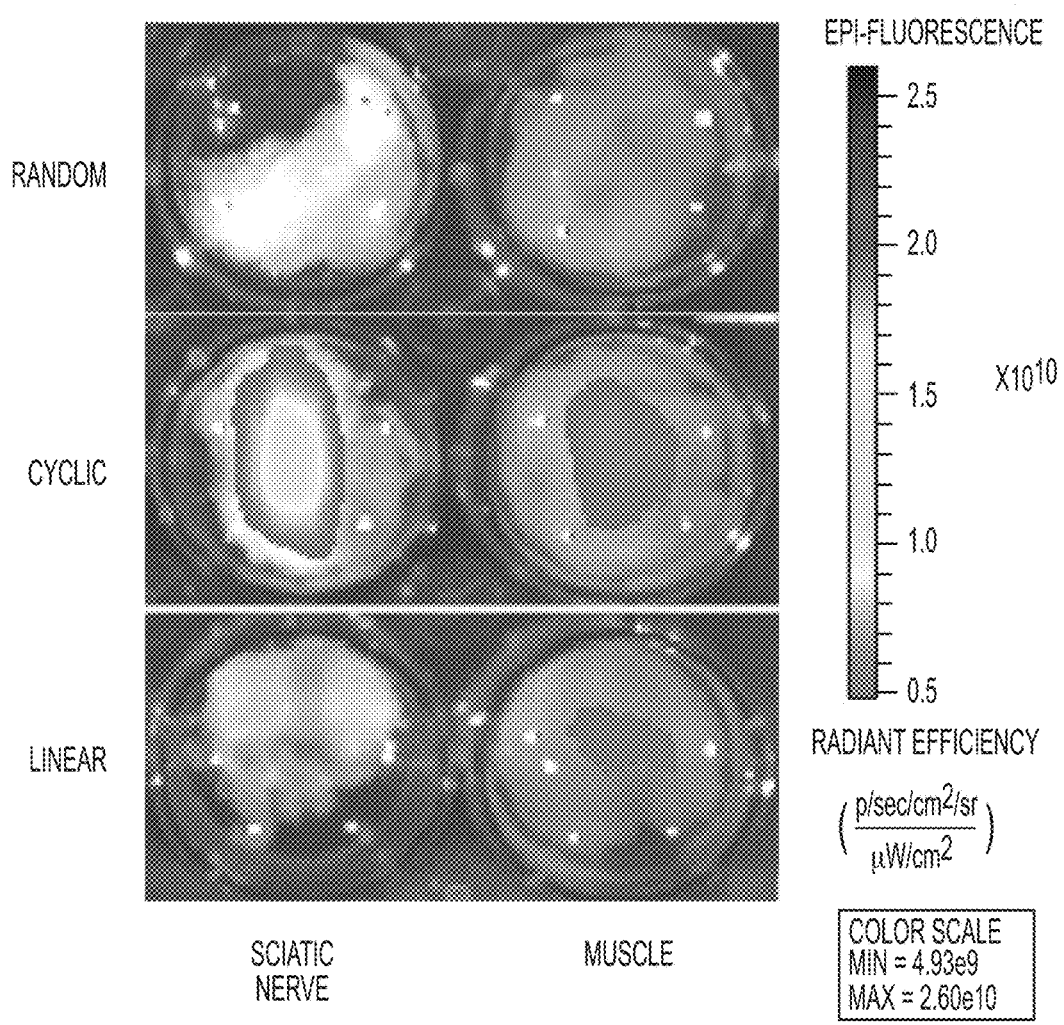
FIG. 2 shows sciatic nerve specimen treated with different confirmation of polypeptides (e.g., Random, Cyclic, linear). Nerve samples were incubated with 50 µM of polypeptide for 30 min. at room temperature, and washed with PBS, three times. Images were obtained on an in vivo imaging system (IVIS) system. Experiment was run in duplicate.

First, the linear polypeptide NP41 was synthesized and labeled with the NIR dye Cy5 for testing. The structure shown in FIG. 1A was confirmed by LCMS, as shown in FIG. 1C. A cyclic analogue of the NP41 structure of FIG. 1A was also synthesized. The structure of the cyclic peptide shown in FIG. 1B was also confirmed by LCMS, as shown in FIG. 1D. As a control, a random polypeptide (Ac-SHSSTARDLWPHGKEGC (SEQ ID NO: 5)) was labeled with Cy5 and assessed. As shown in FIG. 2, the cyclic compound exhibited significantly enhanced fluorescence intensity (2 to 3-fold) compared to the scrambled and linear polypeptides for a sciatic nerve specimen. The cyclic compound also exhibited enhanced nerve tissue selectivity (vs. muscle tissue) as compared with both the linear and scrambled polypeptides FIGS. 4A-4H show synthesis and characterization of different peptide-dye conjugate confirmations (e.g., linear, cyclized, scrambled) for nerve binding experiments described herein. For example, synthesized linear and cyclized conformations of 17 amino acid (AA) sequence peptides, truncated sequence peptides (10-AA, 14-AA) and scrambled sequence peptides by solid phase peptide synthesizer. Peptides were labeled with Cy5-maleimide at the cysteine residue in the liquid phase. Final products were purified using prep-HPLC with greater than 95% yield. The purity and mass of final products were characterized and confirmed by analytical HPLC and LC-MS as shown in each table. Final nerve binding peptide products were subsequently attached to C' dots to create multivalent platforms for in vivo and ex vivo studies.

Figure 3:
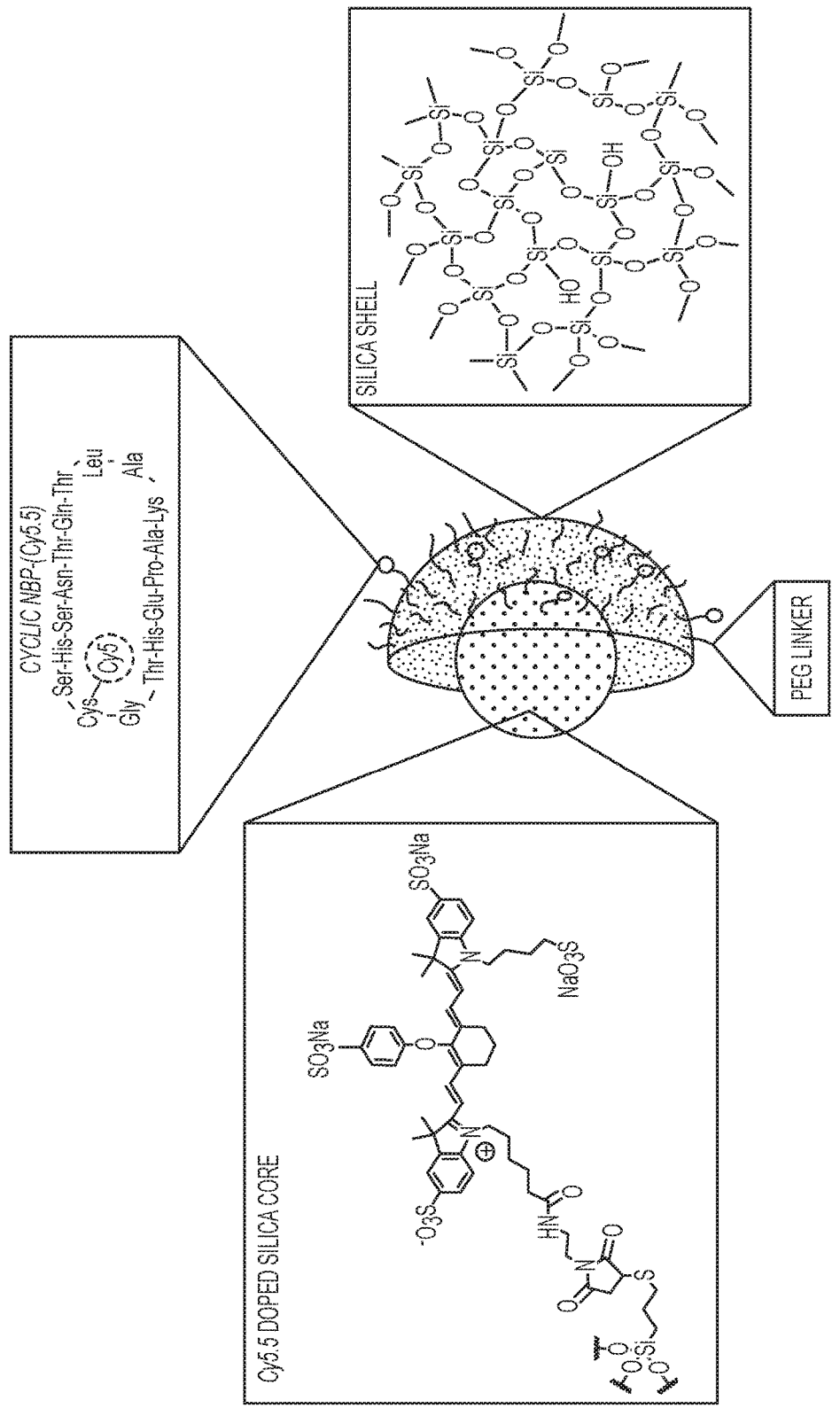
FIG. 3 shows a schematic of nerve binding protein (NBP)-polyethylene glycol (PEG)-Cy5.5-C' dots (SEQ ID NO: 11). Dyes are encapsulated within a silica shell and surface-functionalized with peptides.
Figure 4A:
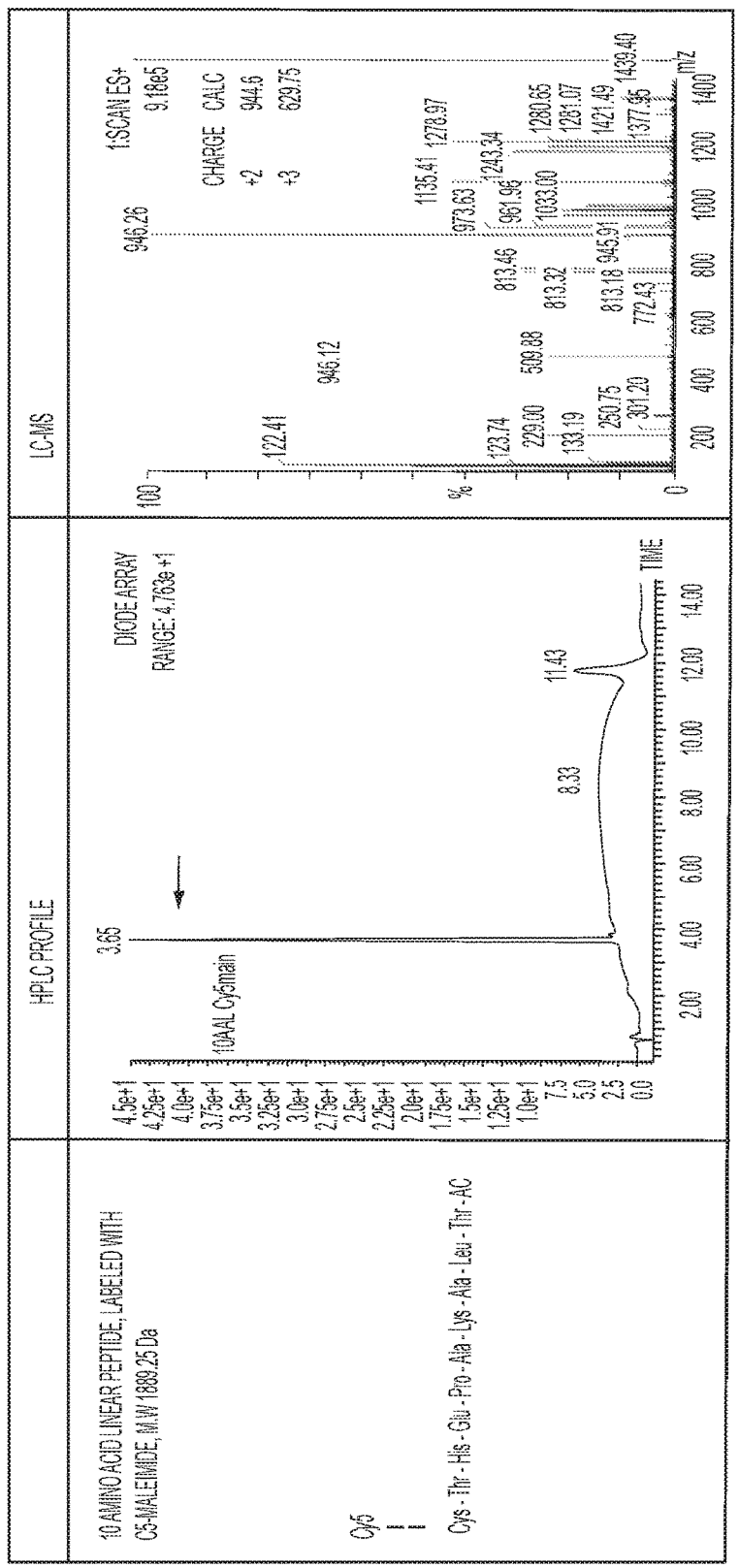
FIGS. 4A-4H show synthesized linear and cyclized conformations of 17 amino acid (AA) sequence peptides, truncated sequence peptides (e.g., 10-AA, 14-AA) and scrambled sequence peptides by solid phase peptide synthesizer. HPLC profile and characterization using LC-MS are also shown.
Figure 4B:
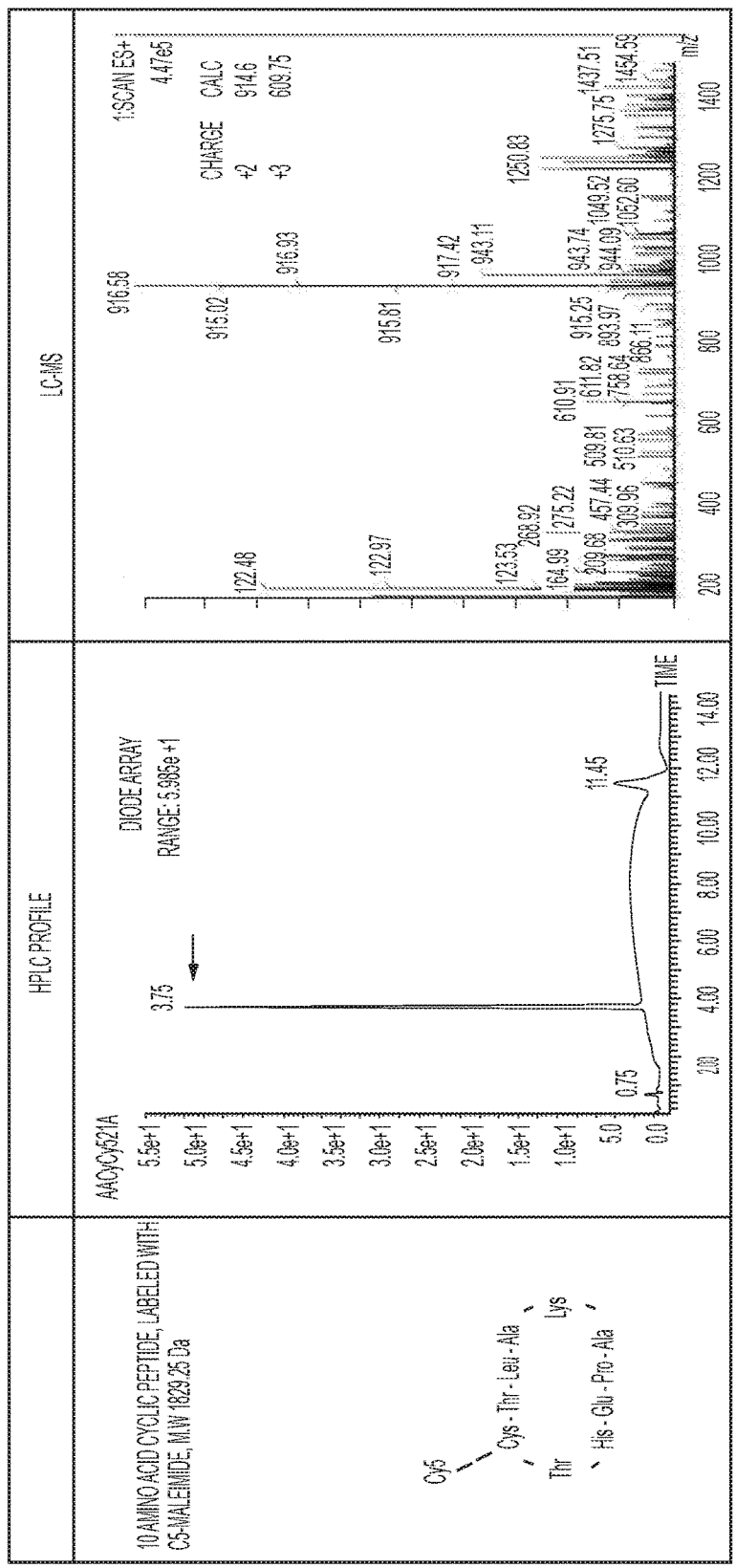
Figure 4C:
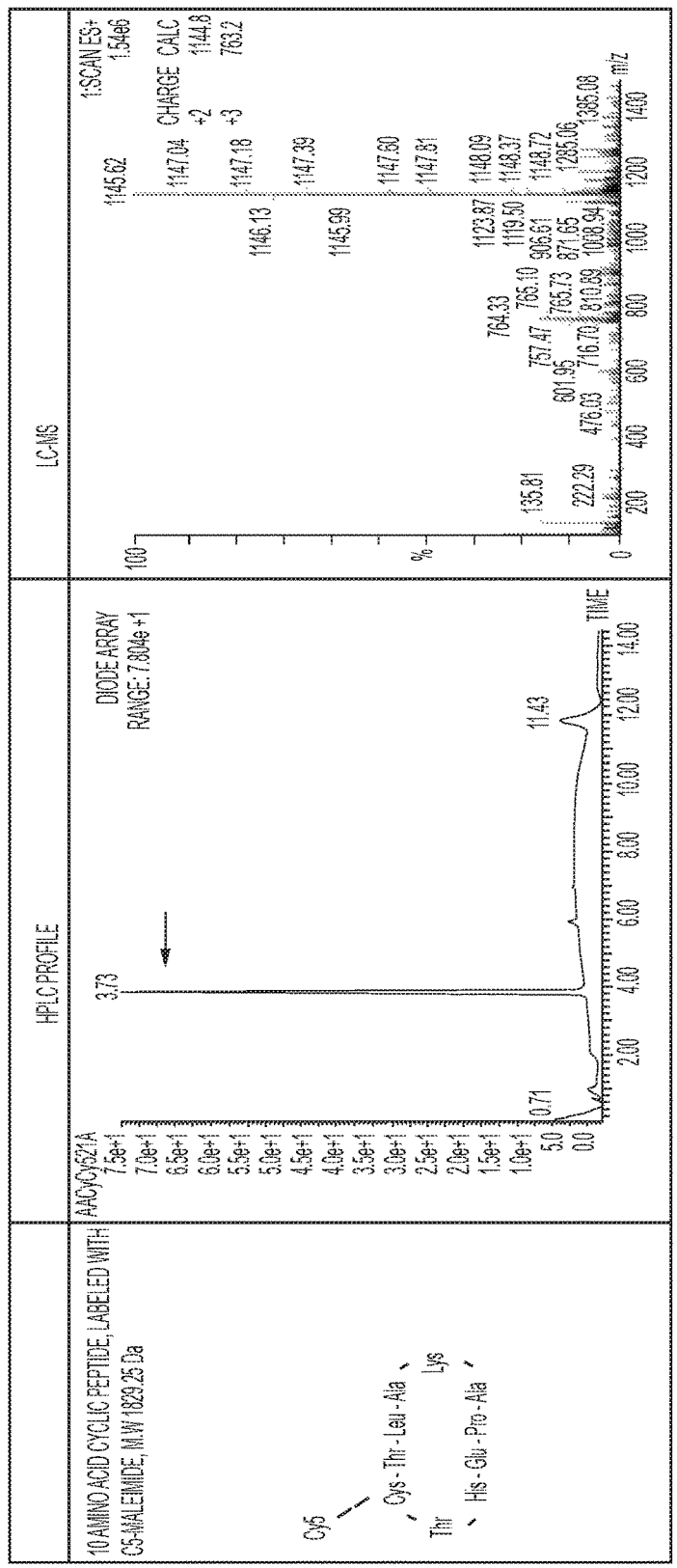
Figure 4D:
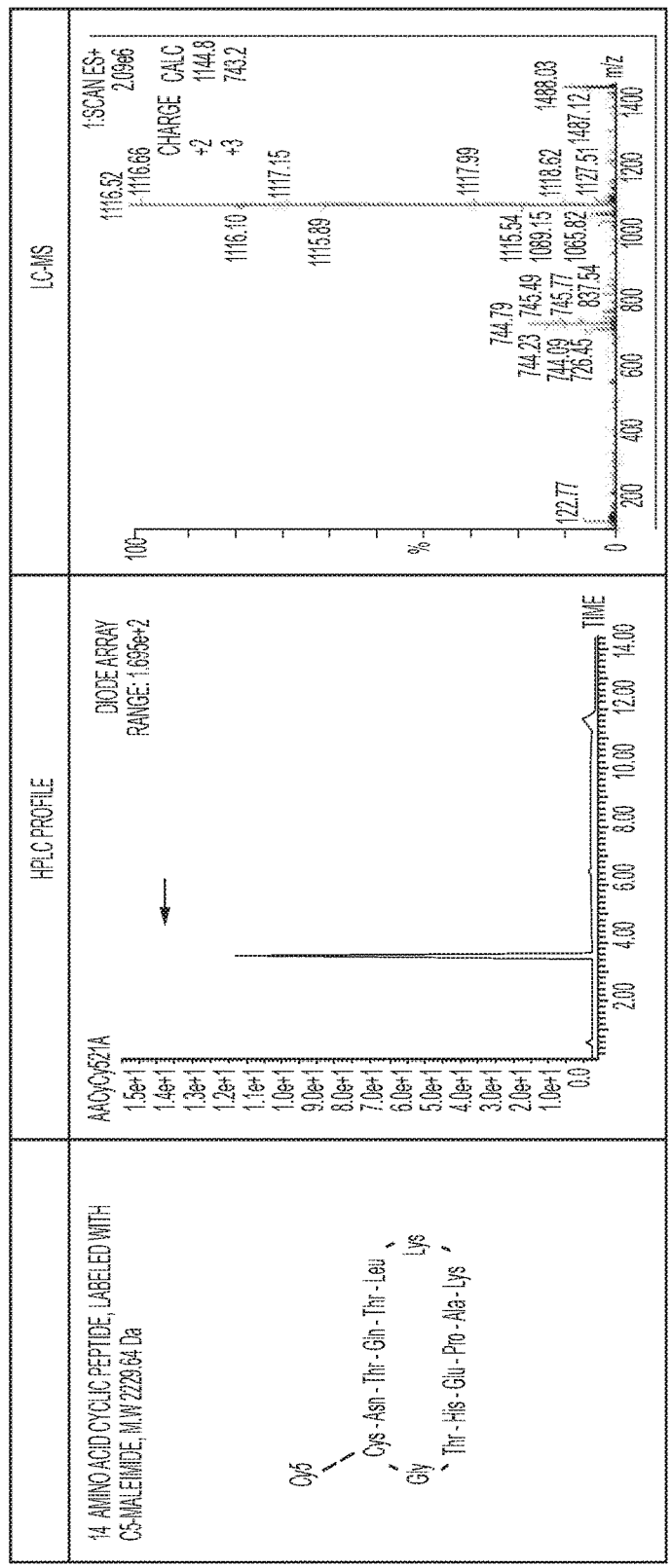
Figure 4E:
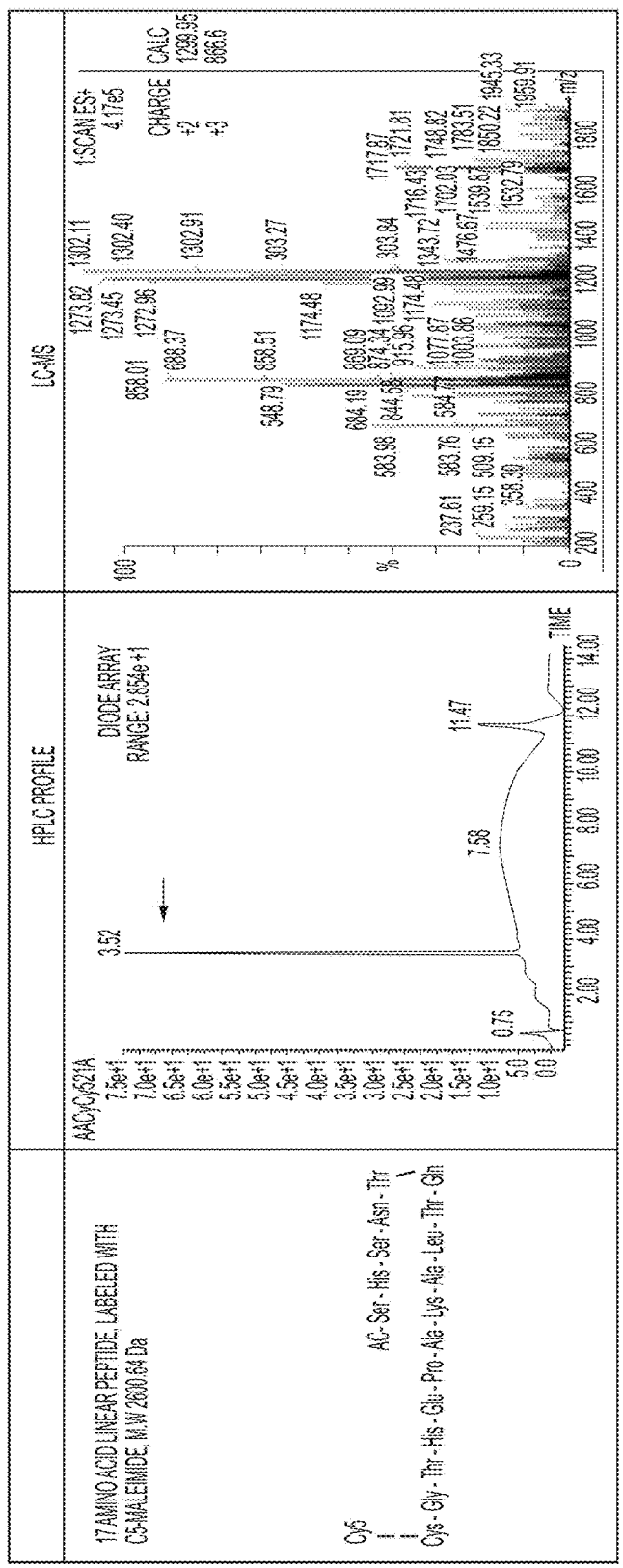
Figure 4F:
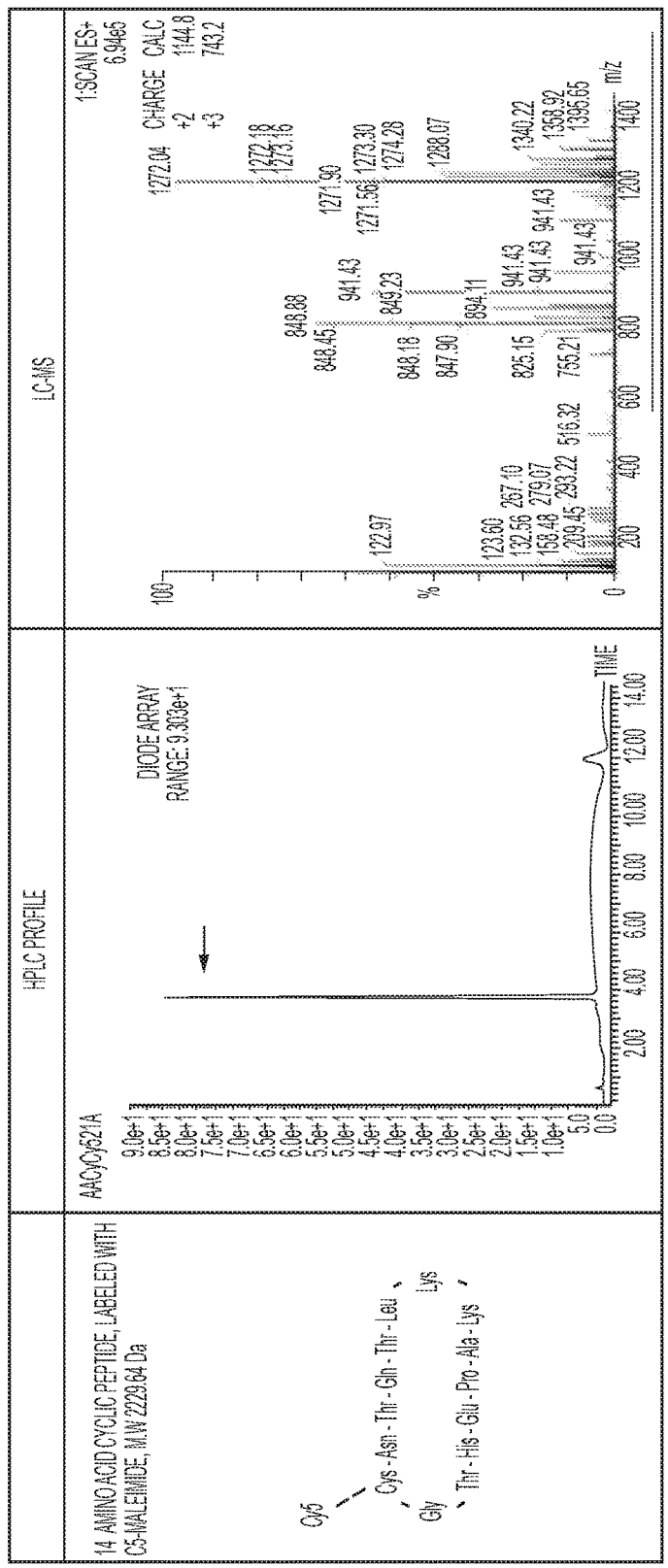
Figure 4G:
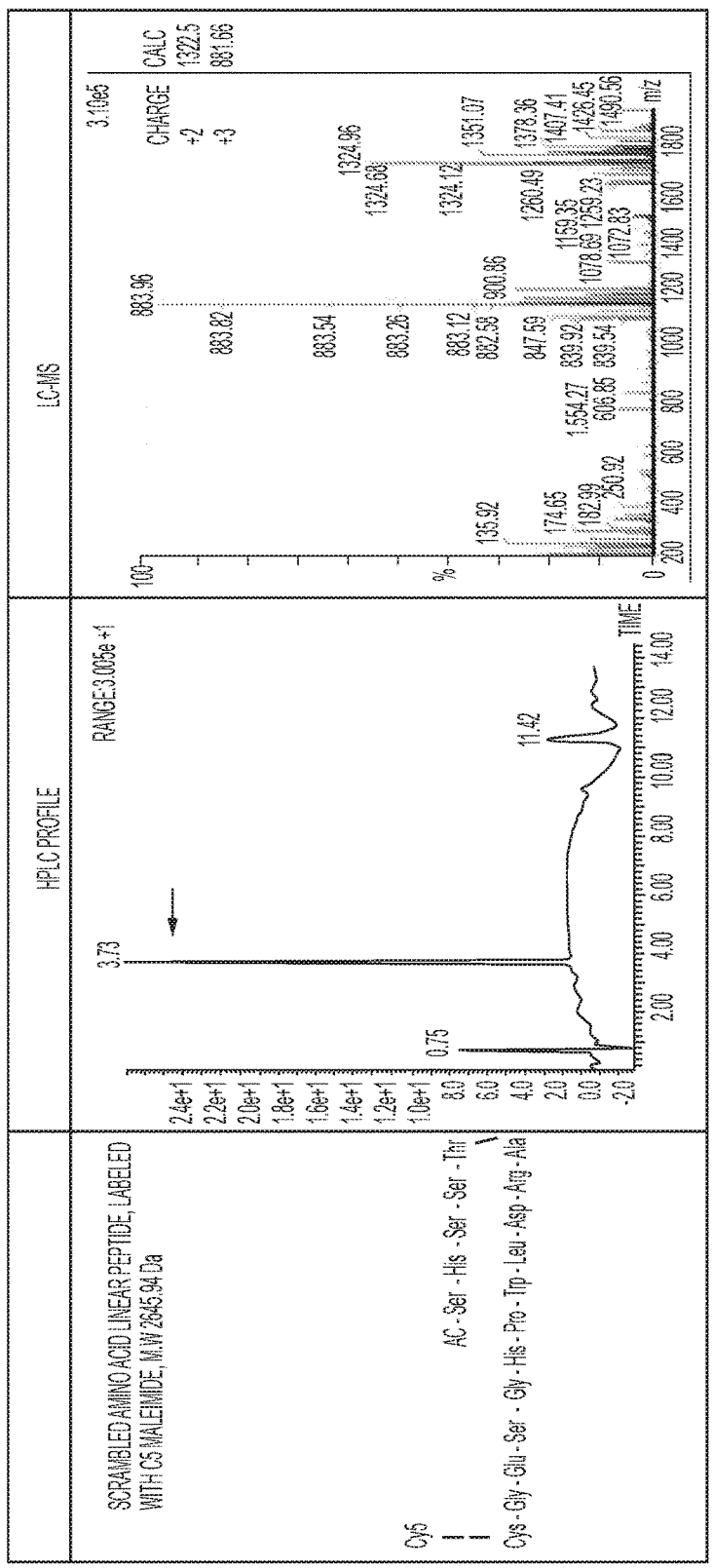
Figure 4H:
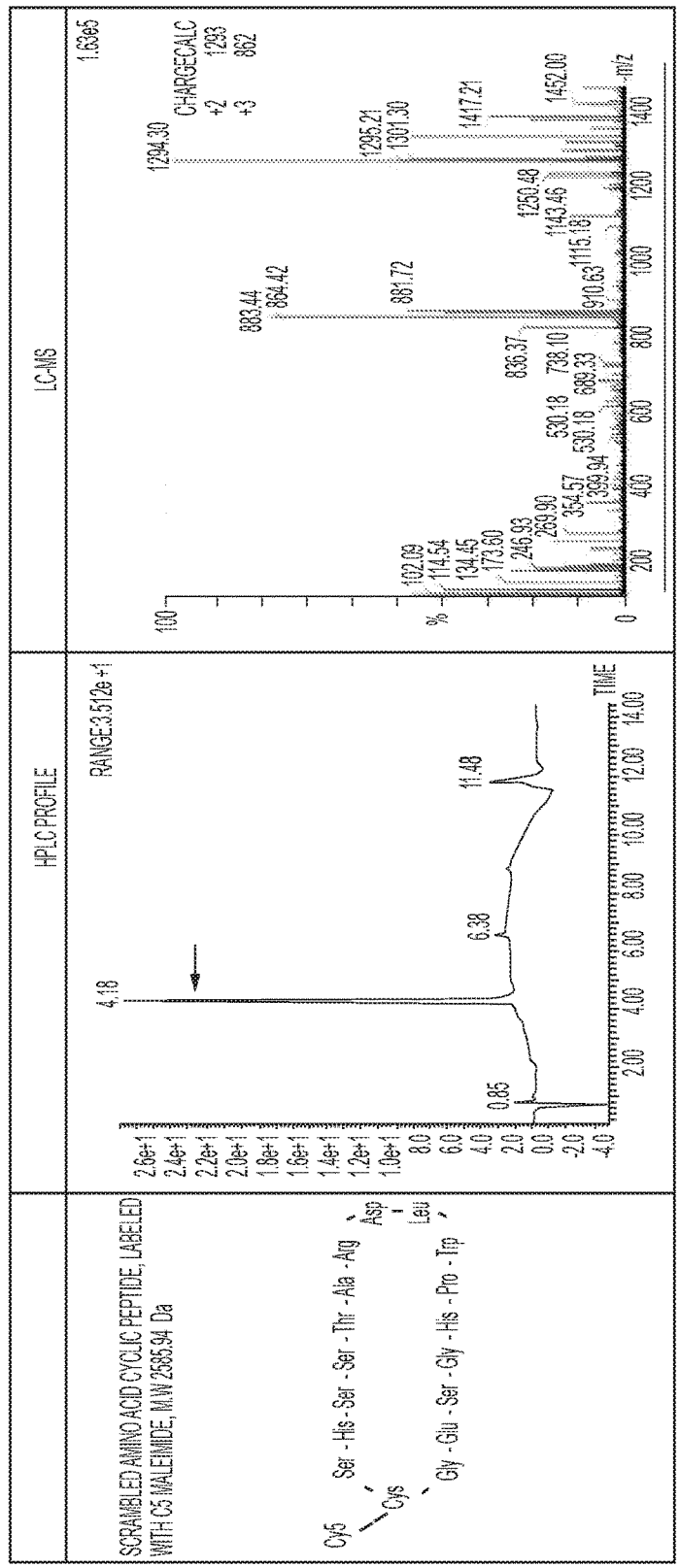

To improve quantum enhancement and fluorescence correlation spectroscopy (FCS) brightness, the cyclic compound may be bound (or otherwise incorporated) onto/into nanoparticles, for example, C dots as described by Phillips (Phillips E, Penate-Medina O, Zanzonico P B, Carvajal R D, Mohan P, Ye Y, Humm J, Gönen M, Kaliagian H, Schöder H, Strauss W, Larson S M, Wiesner U, Bradbury M S. Clinical Translation of an Ultrasmall Optical Hybrid Nanoparticle Probe. Science Translational Medicine. 2014; 6(260)) and/or C'dots, a newer generation PET radiolabel ($^{124}$I) FDA-IND approved cRGDY-functionalized C'dot incorporating Cy5.5 ("RGDY" disclosed as SEQ ID NO: 17). Fluorescent silica precursors are developed by coupling a reactive dye species with an organosilicate source. The hybrid precursors are then hydrolyzed and condensed with pure silica to yield hybrid organic/inorganic cores. These cores act as heterogeneous nuclei for the growth of a pure silica shell, further protecting the encapsulated dyes. (Burns, A., OW, H., Wiesner, U. Fluorescent core-shell silica nanoparticles: towards "Lab on a Particle" architectures for nanobiotechnology. Chem Soc Rev. 2006; 35(11):1028-42) (FIG. 3). Core-shell nanoparticles with fluorescent cores are also described in U.S. Pat. Nos. 8,298,677 and 8,409,876, which are hereby incorporated by reference in their entireties.

In certain embodiments, features described in Bradbury et al. Integr. Biol. (2013) 5:74-86, which is hereby incorporated herein by reference, may be used. In certain embodiments, features (e.g., probe species) described in Herz et al. J. Mater. Chem. (2009) 19, 6341-6347, which is incorporated herein by reference, can be used.

In certain embodiments, features (e.g., nanoparticles) described in Bradbury et al., International PCT patent application numbers PCT/US2010/040994 and PCT/US2014/030401, published as WO2011/003109 on Jan. 6, 2011, and WO2014/145606 on Sep. 18, 2014, which are both hereby incorporated herein by reference in their entireties, can be used.

In certain embodiments, features (e.g., nanoparticles) described in Wiesner et al., U.S. Pat. No. 8,298,677, published on Oct. 30, 2012, which is hereby incorporated herein by reference in its entirety, can be used.

FIG. 3 shows a schematic of NBP-PEG-Cy5.5-C' dots, in accordance with an illustrative embodiment of the invention. NBP is a particular cyclic nerve-binding peptide described in further detail herein below. The Cy5.5 dye is shown as appending to the cyclic NBP structure, and Cy5.5 is also shown as being doped in the silica core. In certain embodiments, dye is attached to the cyclic peptide and not attached, contained within, bound to, or otherwise directly associated with the nanoparticle. In certain embodiments, dye is not attached to the cyclic peptide but is attached, contained within, bound to, and/or otherwise directly associated with the nanoparticle.

To demonstrate signal enhancement over the background, the linear polypeptide NP41 was bound to C'dots via PEG conjugation, and resulting improvement in quantum enhancement and FCS brightness was measured (Table 1). Similarly, cyclic peptide(s) can be bound to nanoparticles for improved quantum enhancement and FCS brightness over the non-bound cyclic peptide.

Table 1 shows Characterization Data of Linear NBP-C'dots. Measurements were determined from fluorescence correlation spectroscopy (FCS).

TABLE 1

| | Hydrodynamic Diameter | Quantum Enhancement | # of Cy5 per particles | FCS Brightness | # of NBP per particles |
|---|---|---|---|---|---|
| Cy5 | 1.4 nm | 1 | 1 | 9.2 kHz | — |
| CyclicNBP-Cy5 | 2.2 nm | 0.9 | 1 | 9.0 kHz | 1 |
| LinearNBP-Cy5 | 2.4 nm | 0.9 | 1 | 8.9 kHz | 1 |
| LinearNBP-PEG-Cy5-C'dot (low ligand density) | 6.2 nm | 1.4 | 1.9 | 23.5 kHz | ~5 |
| LinearNBP-PEG-Cy5-C'dot (medium ligand density) | 6.9 nm | 1.3 | 2.0 | 23.4 kHz | ~10 |
| LinearNBP-PEG-Cy5-C'dot (high ligand density) | 7.6 nm | 1.3 | 2.3 | 27.7 kHz | ~20 |

Phage display approaches can be used to identify novel human nerve binding peptide sequences (e.g., nerve-selective markers) specific to human cadaveric nerve tissue specimens. Phage display, a powerful genetic tool successfully applied to excised murine nerve tissue, can be used with human facial and laryngeal nerve specimens to identify novel NBP sequences with selectivity to these nerve tissues. Peptide sequences exhibiting favorable overall binding affinities and selectivities to nerve tissue can be used for multiplexing applications after attachment to C dots.

In certain embodiments, phage display utilizes a combinatorial library of random 12-residue peptides, with a complexity of 109 independent clones or sequences (New England BioLabs). The m13 phage vector provides a pentavalent display of random peptides fused to the pIII coat protein. Phage undergo multiple rounds of positive and negative selection. Phage that bind prepared facial (or laryngeal) nerve tissues are positively selected through isolation, sequencing, and amplification. Phage then undergo a negative selection step; it will be incubated with sciatic tissue and non-binding phage selected. This selection cycle can continue until distinct sequences are repeatedly observed.

As described herein, experiments were conducted with the linear polypeptide NP41, which includes the sequence NTQTLAKAPEHT (SEQ ID NO: 6), or, more specifically, Ac-SHSNTQTLAKAPEHTGC (SEQ ID NO: 7), as well as a cyclic form of the polypeptide (shown in FIG. 1B). Each polypeptide was functionalized with a fluorescent dye. In certain embodiments, other detectable markers can be used, and other peptide sequences can be used. The core sequence of NP41 is NTQTLAKAPEHT (SEQ ID NO: 6). While the NP41 polypeptide used in the experiments includes an acetyl-SHS-group attached to the N-terminus and a -GC group attached to the C-terminus, other embodiments can use other end groups (or no end groups). In the example shown, the —SHS— group is included from the phage coat protein, and -GC is included for the dye. Without wishing to be bound by any particular theory, it appears that chemically constraining the linear form of the polypeptide enhances binding. Other polypeptides with nerve tissue selectivity could also be used as-is, bound to nanoparticles, cyclized, and/or cyclized and bound to nanoparticles, e.g., the latter by using suitable linker chemistries (e.g., PEG). For example, other polypeptides that can be used, cyclized, and/or bound to nanoparticles include the linear polypeptides in Whitney et al., such as polypeptides comprising the sequences TYT-DWLNFWAWP (SEQ ID NO: 8); NTQTLAKAPEHT (SEQ ID NO: 6); KSLSRHDHIHHH (SEQ ID NO: 9); and/or DFTKTSPLGIH (SEQ ID NO: 10).

In certain embodiments, other polypeptides are used. For example, any of the sequences disclosed herein may be added to, modified, or reduced in length. While the experiments described herein form head-to-tail cyclic peptides using amide chemistry, the covalent constraint may be introduced internally (e.g., as opposed to head-to-tail), and/or other chemistries would also work (e.g., click, disulfide, metathesis, etc.). In certain embodiments, the polypeptide has from 5 to 20 amino acid residues and/or a 15 atom to 60 atom macrocycle (e.g., number of atoms forming the ring, e.g., 15- to 60-member ring).

In general, nanoparticles used in the practice of embodiments described herein are silica-based nanoparticles, for example, C dots or C'dots, which are infused with, coated with, or otherwise bound or associated with a detectable agent, (e.g., organic dye, radiolabel) and peptide targeting ligand(s). In certain embodiments, the silica-based nanoparticles, for example the C dots or C' dots, may have an average size (e.g., diameter) of less than or equal to 10 nm, prior to functionalization with a peptide. In certain embodiments, the silica-based nanoparticles, for example the C dots or C' dots, may have an average size greater than 10 nm prior to functionalization with a peptide. In certain embodiments, average particle size, particle size distributions, and/or brightness is/are customized for the specific application. In certain embodiments, polymer-based nanoparticles are used. In certain embodiments, the polypeptide-detectable agent-nanoparticle material (nanoparticles with linear or cyclic peptide and detectable agent attached thereto or otherwise associated therewith) is non-toxic and efficiently clears through the kidneys. In certain embodiments a dye is bound to the peptide (rather than directly bound to the nanoparticle). In certain embodiments, a dye is bound to, incorporated within, or otherwise associated with the nanoparticle, rather than the peptide. In certain embodiments, a dye is associated with the nanoparticle, and a dye is bound to the peptide.

In certain embodiments, the silica-based nanoparticles may be surface-functionalized with multiple different polypeptides. In certain embodiments, the multiple polypeptides may be infused with, coated with, or otherwise bound or associated with multiple detection agents that are detectable with distinct read outs. In certain embodiments, the silica-based nanoparticles may be used simultaneously or at different times to perform multiplexed optical detection of targeted ligands for intraoperative use. For example, in certain embodiments, two or more spectrally distinct silica-based nanoparticles, each containing a unique surface-functionalized targeting ligand, can be used to create multivalent structures for intraoperative use. In certain embodiments, spectrally distinct silica-based nanoparticles, each containing a unique surface-functionalized targeting ligand, may emit signatures measurable by distinct detection modalities, creating multi-modal readout functionalities.

The systems and methods described herein can be used with systems and methods described in U.S. patent application Ser. No. 13/381,209, published as US 2013/0039848 on Feb. 14, 2013, which relates to in vivo imaging systems and methods employing a fluorescent silica-based nanoparticle, and is incorporated by reference. In some embodiments, at least one of the probe species comprises nanoparticles. In some embodiments, the nanoparticles have a silica architecture and dye-rich core. In some embodiments, the dye rich core comprises a fluorescent reporter. In some embodiments, the fluorescent reporter is a near infrared or far red dye. In some embodiments, the fluorescent reporter is selected from the group consisting of a fluorophore, fluorochrome, dye, pigment, fluorescent transition metal, and fluorescent protein. In some embodiments, the fluorescent reporter is selected from the group consisting of Cy5, Cy5.5, Cy2, FITC, TRITC, Cy7, FAM, Cy3, Cy3.5, Texas Red, ROX, HEX, JA133, AlexaFluor 488, AlexaFluor 546, AlexaFluor 633, AlexaFluor 555, AlexaFluor 647, DAPI, TMR, R6G, GFP, enhanced GFP, CFP, ECFP, YFP, Citrine, Venus, YPet, CyPet, AMCA, Spectrum Green, Spectrum Orange, Spectrum Aqua, Lissamine and Europium.

In certain embodiments, fluorescent agent(s) have excitation and emission wavelengths in the red and near infrared spectrum in the range. In certain embodiments, fluorescent agent(s) have excitation and emission wavelengths ranging from 400 to 1300 nm, or from 440 to 1100 nm, or from 550 to 800 nm, or from 600 to 900 nm. Use of this portion of the electromagnetic spectrum maximizes tissue penetration and minimizes absorption by physiologically abundant absorbers such as hemoglobin (<650 nm) and water (>1200 nm). Probe species with excitation and emission wavelengths in other spectrums, such as the visible and ultraviolet light spectrum, can also be employed in certain embodiments. In particular, fluorophores such as certain carbocyanine or polymethine fluorescent fluorochromes or dyes can be used as the fluorescent agent, e.g., U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060

B1, WO 98/47538, WO 00/16810, EP 1 113 822 B1, WO 01/43781, EP 1 237 583 A1, WO 03/074091, EP 1 480 683 B1, WO 06/072580, EP 1 833 513 A1, EP 1 679 082 A1, WO 97/40104, WO 99/51702, WO 01/21624, and EP 1 065 250 A1; and Tetrahedron Letters 41, 9185-88 (2000).

Exemplary fluorescent agents include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-5680, VivoTag™-5750 (VisEn Medical); Dy677, Dy682, Dy752 and Dy780 (Dyomics); DyLight® 547, and/or DyLight® 647 (Pierce); HiLyte Fluor™ 647, HiLyte Fluor™ 680, and HiLyte Fluor™ 750 (AnaSpec®); IRDye® 800CW, IRDye® 800RS, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health). In certain embodiments, a linker moiety is a chemical moiety with two or more functional groups at terminal ends (bifunctional, trifunctional, etc.) arranged to connect a silica-based nanoparticle with a peptide and/or detectable marker. In the experimental examples described herein, PEG was used as linker moiety to bind the polypeptide (e.g., linear or cyclic peptide) to the nanoparticle. Other linker moieties can be used. Spacing between C'dot (or other nanoparticle) and polypeptide can be varied using different sized PEG (or other linker) chains, for example. In certain embodiments, the linker moiety comprises one or more of the linker moieties described in U.S. patent application Ser. No. 14/722,307, filed May 27, 2015, published as U.S. Patent Application Publication No. US 2015/0343091, the text of which is incorporated herein by reference in its entirety.

In certain embodiments, nerve binding peptide-functionalized C dots or peptide-dye conjugates have different conformations (e.g., cyclic, linear) and lengths (e.g., truncated, elongated), and are administered topically to peripheral nerve trunks adjacent to or within the vicinity of metastatic lymph nodes or primary tumors after surgical exposure, including, but not limited to, the facial, sciatic, hypogastric, laryngeal, nerves in order to significantly enhance contrast and delineate small, distal nerve branches and/or distributions during SLN mapping procedures not well visualized in the absence of these agents to reduce risk of injury.

In certain embodiments, these peptide-functionalized particle probes or peptide-dye conjugates may be locally administered about the primary tumor site or diseased nodes (e.g., parotid gland) in order to facilitate their uptake by adjacent normal nerves e.g., facial).

In certain embodiments, the substance or formulation is administered via local injection vs. IV administration. For example, substances or formulations with peptide-containing compositions (e.g., both particle-containing and non-particle-containing compositions) can be locally injected in a sufficiently high concentration for imaging purposes. In certain embodiments, non-particle peptide-containing compositions are administered via IV. In certain embodiments, local injection is preferred over IV injection when particle-containing compositions are too viscous at concentrations high enough for imaging purposes.

New cyclic peptide or particle-based products can offer improved photophysical and nerve binding properties compared with currently described compounds.

In certain embodiments, nerve binding peptide-functionalized C dots administered via one or more of these routes permit neural structures to be maximally visualized with high nerve-to-muscle contrast, as against that achievable by injection of simple fluorescent dyes alone, due to their superior multivalency enhancement, improved target site binding/retention, and photophysical features. These products can be compatible for use in multiplexing applications alongside peptide-bound particle probes directed to cancer targets (e.g., cancer-bearing nodes).

In certain embodiments, a visible dye (e.g., a dye in the visible spectrum, e.g., a green dye, e.g., FITC) can be administered locally or via IV and can be used to see the nerve by fluorescent signal. In certain embodiments, the peptide-bound visible dye attaches preferentially to nerve tissue and light from the dye can be seen with the surgeon's own sight. For example, the formulation may be applied topically to the nerve itself or locally near the nerve, e.g., the formulation may be topically applied to a peripheral nerve trunk (e.g., adjacent to or within the vicinity of a metastatic lymph node or primary tumor after surgical exposure), allowing the composition of the formulation to diffuse from the nerve trunk to smaller branches of the nerve tissue. Light is emitted by the fluorescent agent of the composition, and can be detected and displayed (e.g., in real time), or may be sufficiently bright for direct viewing by a surgeon with her own unaided eyesight during a surgical procedure. Topical application to nerve tissue (and subsequent diffusing through the nerve tissue) may provide greater contrast, since background signal from blood proteins (e.g., hemoglobin) would be reduced, as compared to intravenous administration of the formulation.

Experimental Examples

Synthesis of Linear and Cyclic Nerve Binding Polypeptide-Cy5 Conjugates

The linear NP41 (FIG. 1A) and its cyclic analogue (FIG. 1B) were synthesized on chlorotrityl resin using standard Fmoc-based solid-phase peptide synthesis (SPSS) protocols. The linear polypeptide was obtained by cleavage/deprotection of the peptide-resin with a cocktail of TFA:TIS:EDT:water (85:5:5:5), followed by reversed-phase HPLC purification. To prepare the cyclic analogue, the N-terminal Fmoc group was removed, and the fully protected linear polypeptide was then cleaved off resin under mild conditions using hexafluoroisopropanol. The head-to-tail cyclic analogue was obtained by an intramolecular coupling reaction where the N- and C-terminal residues are joined in solution providing the desired cyclic precursor. The crude material was then globally deprotected and purified by reversed-phase HPLC. Using this synthetic approach, the desired 51 membered macrocyclic peptide product was readily obtained. It should be noted that cyclic peptides of this size are synthetically challenging. However the approach used here provided a cyclic product with excellent purity (e.g., greater than 95%) and good yield (~40%). Both linear and cyclic peptides were fluorescently labeled by modifying the free thiol of the cysteine residues with a maleimido-Cy5. The final products were characterized and confirmed by LCMS as shown in FIGS. 1A to 1D.

Synthesis of Linear Polypeptide-Nanoparticle Conjugates (Linear NBP-C'Dot)

The linear nerve binding polypeptide (NBP) NP41 was incorporated onto C'dots using a PEG linker moiety. As shown in Table 1, the measured brightness of the Cy5 dye is at least 130% greater for the NBP-C'dot than for the free polypeptide.

Binding to Ex Vivo Human Sciatic Nerve Tissue

Linear and cyclic peptides, along with a random control polypeptide (Ac-SHSSTARDLWPHGKEGC (SEQ ID NO: 5)), were labeled with Cy5 and assessed for binding to ex vivo human nerve tissue samples. The tissue samples used were cadaveric sciatic nerve freshly excised and obtained by the National Disease Research Interchange (NDRI). Tissue samples were prepared on 24-well plates, washed with PBS, then incubated with 50 uM of either the linear, cyclic, or scrambled polypeptide at room temperature. After 15 min, the samples were subjected to several rounds of washes with PBS. The plates were imaged using an IVIS Spectrum imaging system. As shown in FIG. 2, overall the cyclic compound exhibited significantly enhanced fluorescence intensity (2-3 fold) compared to the scrambled and linear polypeptides for the sciatic nerve specimen; and selectivity over muscle tissue.

Figure 5:
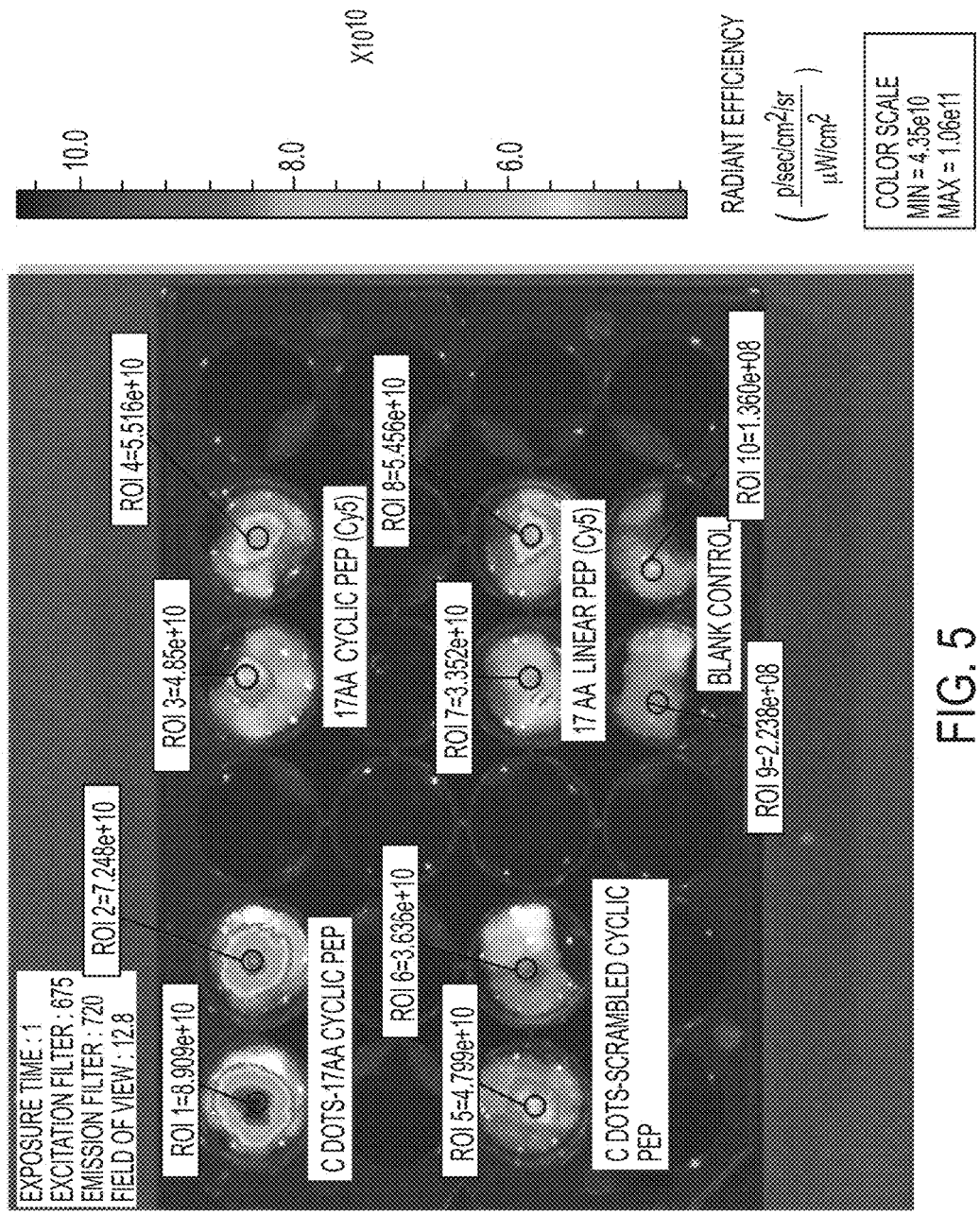
FIG. 5 shows ex vivo binding/uptake studies comparing peptide-NIR dye conjugates to peptide-functionalized deep red/NIR dye-containing (Cy5, Cy5.5) C dots for human cadaveric nerve specimens. The effects of peptide sequence, conformation, and ligand number on nerve binding were tested.

FIG. 5 shows human cadaveric sciatic nerve was sectioned into 1-cm length fragments and incubated in 15 μM solutions of peptides or peptide-bound C dots for 80 minutes at room temperature followed by multiple phosphate buffered saline washings. Non-invasive region of interest analyses obtained 80 minutes post-incubation by IVIS Spectrum imaging, demonstrated increased optical signal (highest to lowest): 17-amino acid (AA) residue peptide-functionalized cyclic C dots (upper left); 17 AA residue cyclic peptide-dye conjugates (upper right); 17 AA residue linear peptide-dye conjugates (middle right); 17 AA scrambled cyclic peptide-functionalized C dots (lower left). The latter two probes served as controls.

Figure 6:
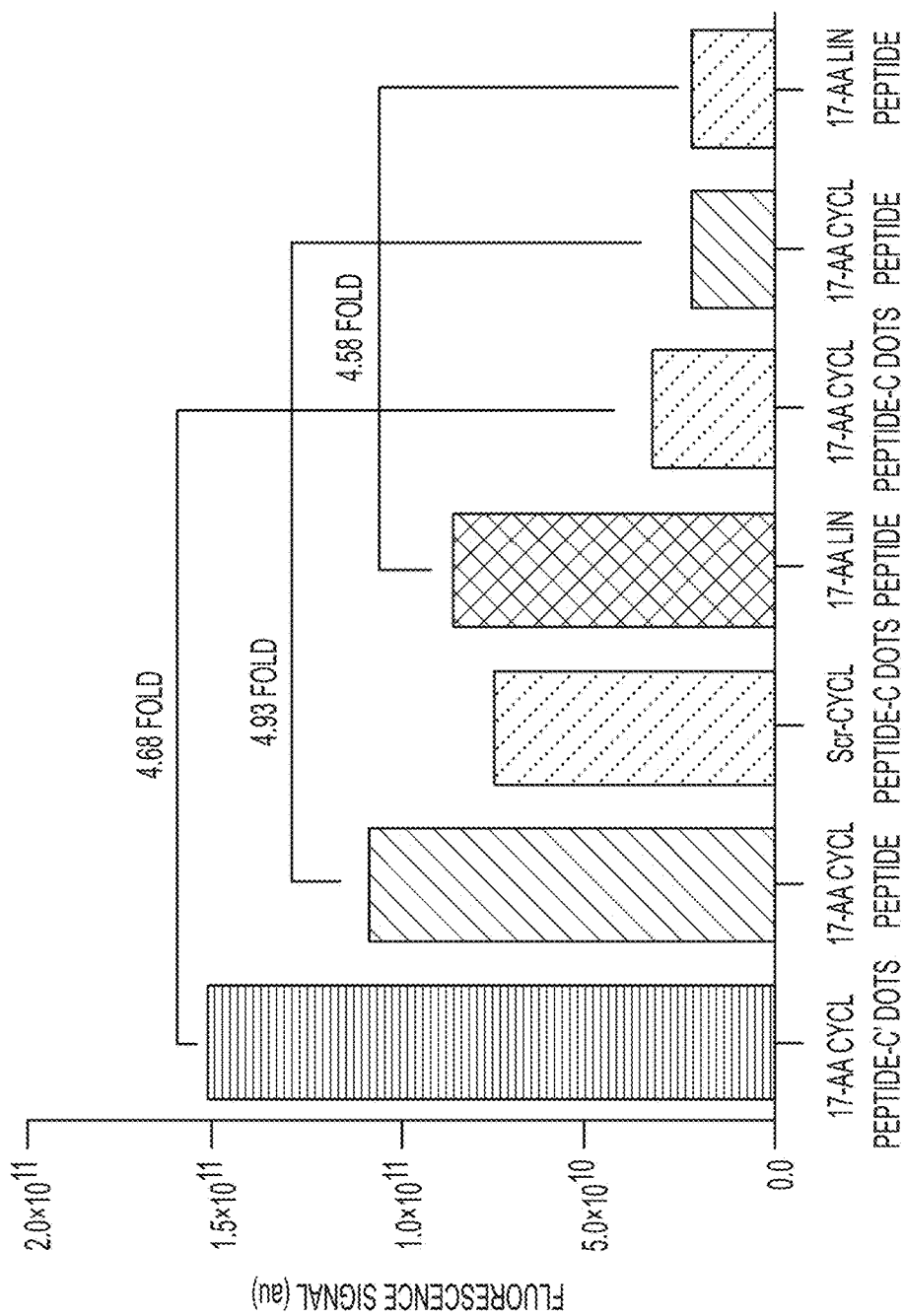
FIG. 6 shows human sciatic nerve and muscle uptake of peptide-dye conjugates or peptide-functionalized C dots.

FIG. 6 shows ex vivo fluorescence signal measurements of nerve and muscle (control) specimens incubated in either peptide-dye conjugates or peptide-functionalized C dot solutions. Nerve and muscle tissue specimens were incubated in 15 μM peptide-dye conjugate or peptide-functionalized C dot solutions for 80 minutes at room temperature with mild shaking followed by PBS washing. Following imaging on the IVIS Spectrum, ROI analysis was performed. Bars indicate mean+/−standard deviation. N=5 per group. Each replicate is from one biological experiment, quantified with five independent fields of view. Higher fluorescence signal was observed in nerve, as against muscle, tissue specimens. Maximum fluorescence signal was measured for 17 AA residue cyclic peptide-functionalized C' dots, followed by 17 AA residue cyclic peptide-dye conjugates, 17 AA residue linear peptide-dye conjugates, and scrambled cyclic peptide-functionalized C dots. At least four- to nearly five-fold greater signal was observed in nerve, compared to muscle tissue specimens incubated with similar probes. Without wishing to be bound to any theory, the data suggest that selective uptake and retention of both peptide-dye conjugates and peptide-functionalized C dots.

Figure 7A:
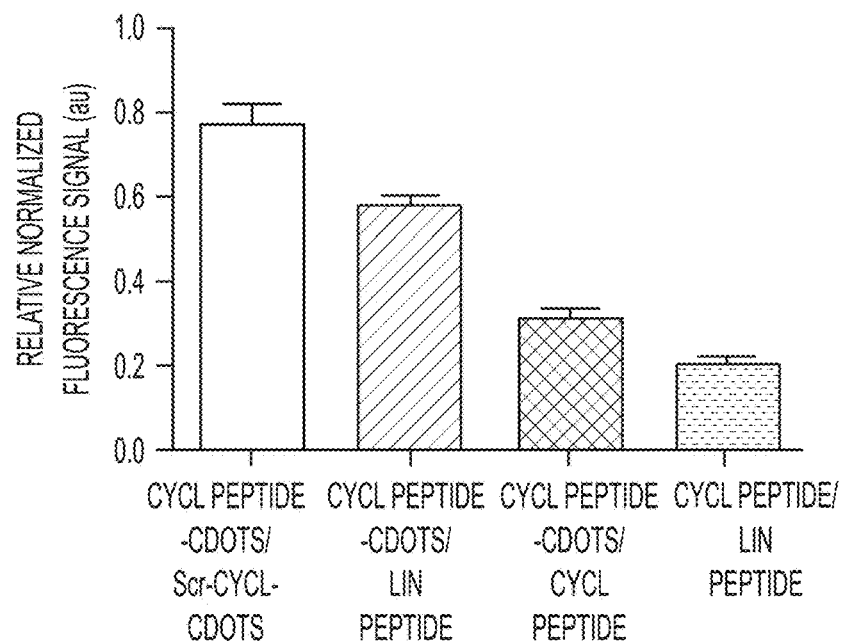
FIGS. 7A and 7B show time varying signal changes in ex vivo human sciatic nerve specimens following incubation with nerve binding peptides or peptide-functionalized C dots using optical imaging methods.
Figure 7B:
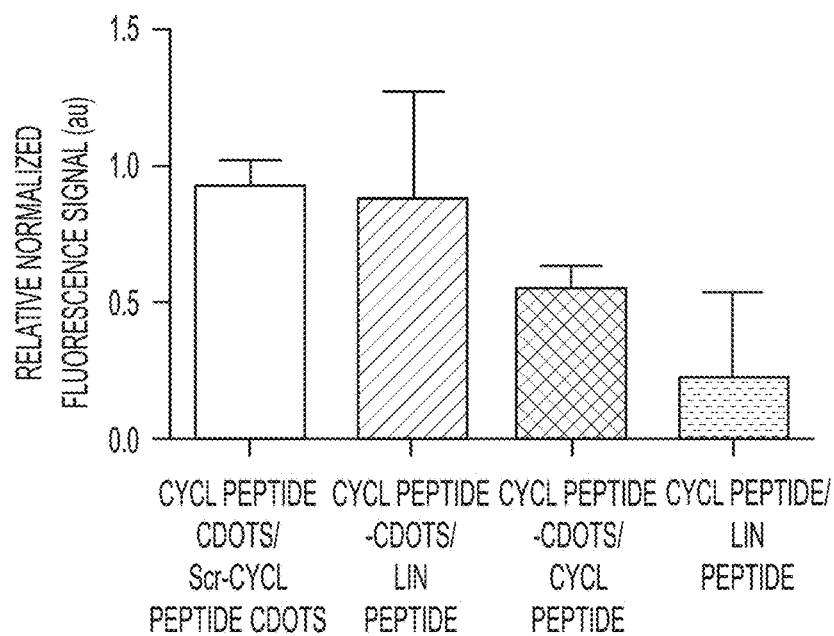

FIGS. 7A and 7B show time-dependent signal changes in uptake following incubation with nerve binding peptides or peptide-functionalized C dots using optical imaging methods. Optical imaging was used to assess time-varying uptake in ex vivo human sciatic nerve specimens incubated with nerve binding peptides (e.g., cyclic, linear, scrambled) or corresponding peptide-functionalized C dots. Bars indicate mean+/−standard deviation. N=5 per group. Each replicate is from one biological experiment, quantified with five independent fields of view. Relative normalized fluorescence signal in incubated nerve specimens was found to be about 80% at 20 min and nearly 100% at 80% relative to the control particle probe (e.g., scrambled peptide-bound C dots). Further, when compared with the native linear peptide, 60% more signal was found at 20 min (e.g., nearly 100% at 80 min) for the 17 AA Cyclic peptide-functionalized C dots.

Figure 8:
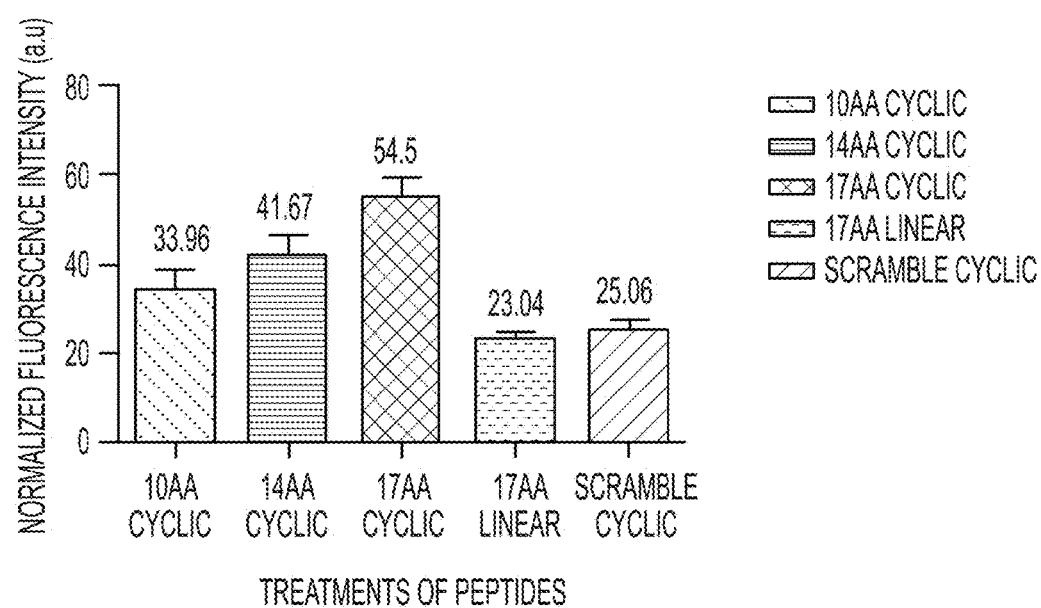
FIG. 8 shows normalized fluorescence signal intensities of human sciatic nerve specimens following incubation with peptide-Cy5 dye conjugates.
Figure 9A:
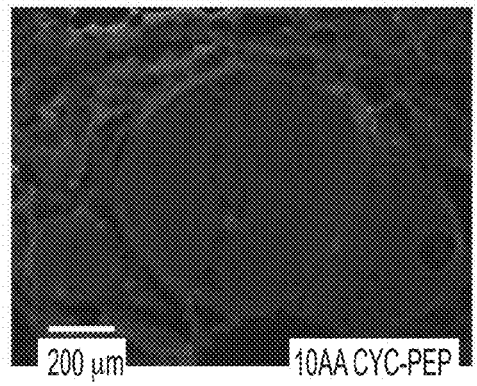
FIGS. 9A-9E show fluorescence microscopy of cryosectioned, peptide-dye conjugates pre-treated human sciatic nerve specimens.
Figure 9B:
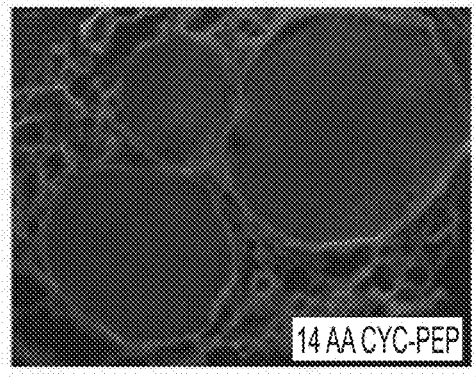
Figure 9C:
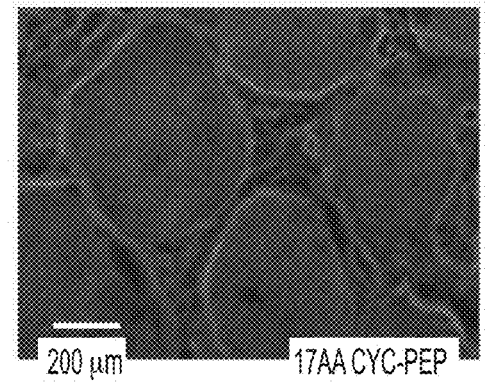
Figure 9D:
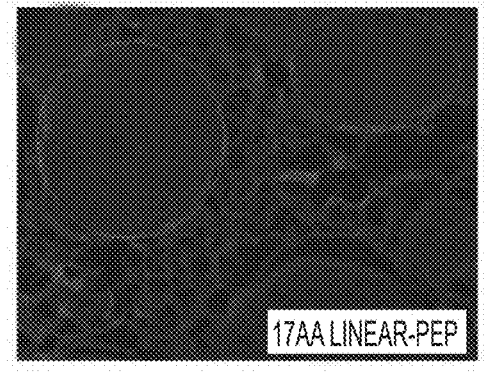
Figure 9E:
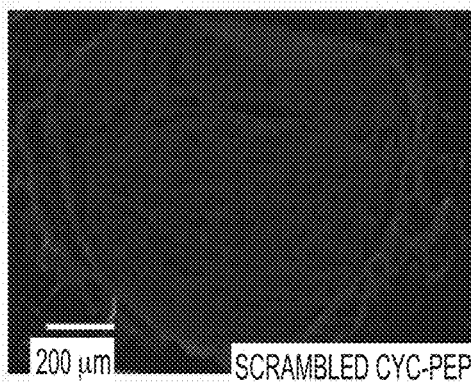

FIG. 8 shows an effect of peptide sequence length and conformation on nerve binding/uptake properties. Human sciatic nerve specimens were incubated in 15 μM solutions of 17 AA, truncated 14-AA, and truncated 10-AA residue peptide sequences having cyclic conformations in order to evaluate the dependence of binding/uptake on sequence specificity and conformation. A linear 17 AA peptide-dye conjugate was used to determine the influence of conformation. The cyclic form of a scrambled sequence peptide was utilized as a control. Bars indicate mean+/−standard deviation. N=5 per group. Each replicate is from one biological experiment, quantified with five independent fields of view. Regions of interest were taken from cross-sectional images. Maximum fluorescence signal was observed using 17 AA cyclic peptide-dye conjugate treatments, followed by that of 14-AA cyclic peptide-dye and 10 AA cyclic peptide-dye conjugates. Greater than a 2-fold change in optical signal was observed with 17 AA cyclic peptide-dye conjugate treatments compared to 17 AA linear peptide-dye conjugate treatments.

FIGS. 9A-9E show an effect of peptide sequence length and conformation on nerve binding/uptake. Selective nerve binding/uptake was assessed following incubation of human sciatic nerve sections with 15 μM peptide-dye conjugate solutions. Pre-incubated nerve tissue was embedded in OCT and cryosectioned in cross-section (20 μm). Maximum fluorescence signal was observed for 17 AA residue cyclic peptide-dye conjugates relative to linear and scrambled peptide constructs using fluorescence microscopy with 5× objective and Cy5 filter set. All Cy5 fluorescence images were acquired at identical exposure and normalization settings. Scale bar=200 μm.

FIGS. 10A-10E show fluorescence signal of nerve specimens incubated with 15 μM nerve binding peptide-functionalized C dots or peptides for 80 minutes. Treated nerve tissue was washed, cryo-sectioned (15 μm) onto slides, and observed by fluorescence microscope (5× objective) (FIGS. 10A-10D). Regions of Interest (ROIs) were placed over the nerve specimen following treatment with different probes. Fluorescence signal (highest to lowest order, see FIG. 10E) was observed in specimens incubated with 17 AA cyclic peptide-functionalized C dots, followed by 17 AA Cyclic or linear peptide-dye conjugates or scrambled cyclic peptide-dye functionalized C dots.

FIGS. 11A and 11B show that inverted microscopy (×20) was used to observe cryo-sectioned sciatic nerve specimens (20 μm) pre-incubated in 17 AA cyclic peptide-dye conjugate solutions (15 μM) for 80 min. FluoroMyelin green (Myelin marker) was used to co-stain nerve sections, followed by PBS washing, and scanning by inverted microscopy (×20). Imaging results show no co-localization of peptide with this myelin marker; the 17 AA cyclic peptide-dye conjugate was observed to primarily involve epineurium and perineurium, while a relatively smaller degree of Cy5 signal was observed within the endoneurium.

Binding to In Vivo Human Sciatic Nerve Tissue

Figure 12:
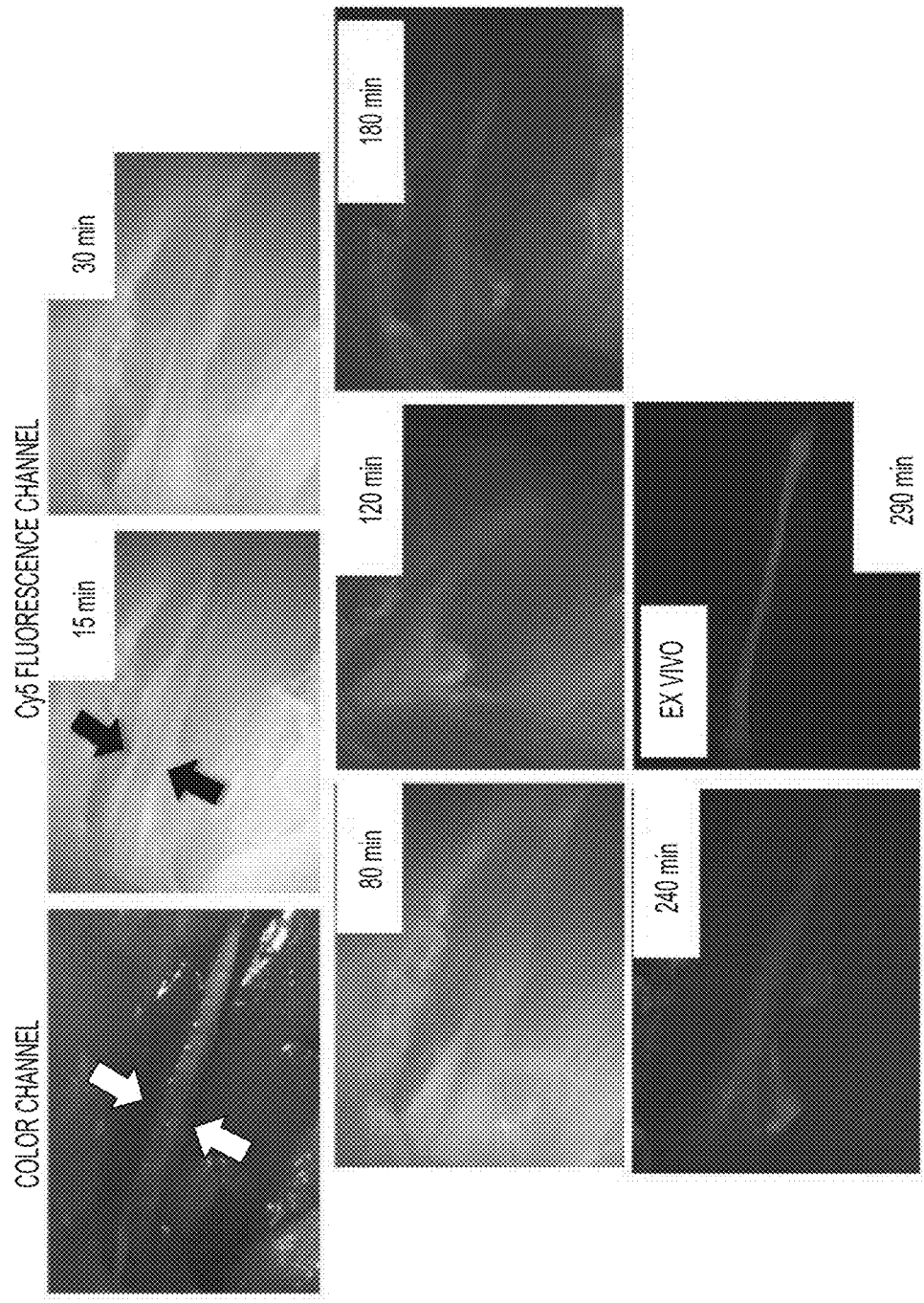
FIG. 12 shows time-dependent in vivo fluorescence microscopy of human sciatic nerve post-injection of 400 nmoles cyclic peptide-dye conjugates.

FIG. 12 shows time-dependent in vivo fluorescence microscopy of human sciatic nerve post-injection of 400 nmoles cyclic peptide-dye conjugates.

Figure 13A:
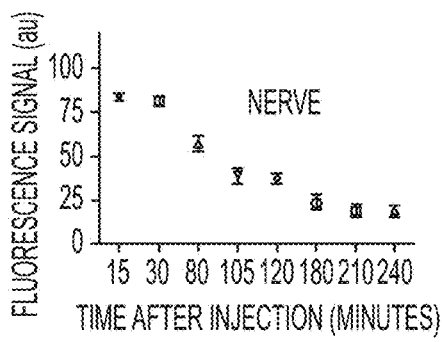
FIGS. 13A-13E show in vivo imaging of sciatic nerve and muscle fluorescence signal versus time post-injection of 17 AA cyclic nerve binding peptides.
Figure 13B:
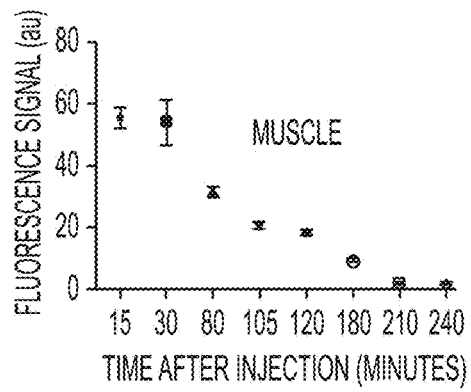
Figure 13C:
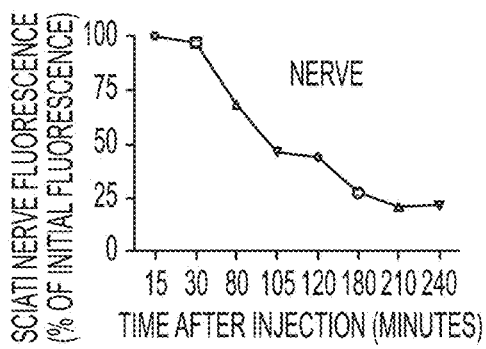
Figure 13D:
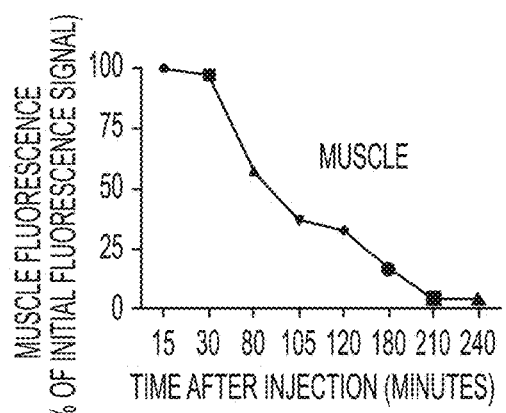
Figure 13E:
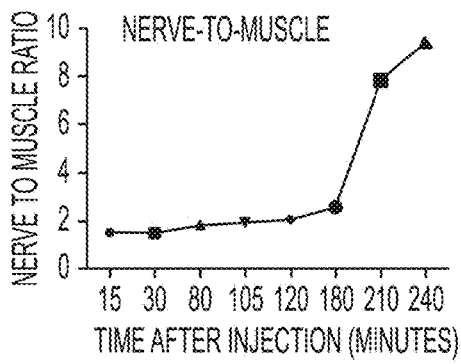

FIGS. 13A-13E show in vivo time-dependent uptake from sciatic nerve and muscle post-iv injection of 17 AA cyclic peptide-dye conjugates using optical imaging. 17 AA cyclic peptide-dye conjugates (Cy5 labeled) were injected intravenously (400 nmole) into the tail veins of nude mouse prior to surgical exposure and imaging of sciatic nerves and adjacent muscle using a Zeiss Lumar stereomicroscope (0.8× objective) with fluorescence imaging capabilities. Pre- and serial post injection (p.i.) images (bright field, fluorescent) were acquired at 8 times points from 15 min to 240 min p.i. Bars indicate mean+/−standard deviation. N=5 per group. Each replicate is from one biological experiment, quantified with five independent fields of view. Region of interest (ROI) analysis was performed over nerve and muscle regions to assess time-dependent signal changes. FIGS. 13A-13E show the absolute and relative fluorescence signal (e.g., percentage of the initial fluorescence signal acquired at 15 min p.i.) of nerves (FIGS. 13A and 13B) and adjacent muscle (FIGS. 13B and 13D), respectively. FIG. 13E shows time-varying nerve-to-muscle or contrast ratios, which increased from about 1.2 to nearly 2.0 over a 4 hour period, suggesting selective uptake and retention by nerve specimens with time.

FIGS. 13A-13E show that the cyclized peptide provides a good fluorescent signal from the nerve in contrast with signal from the (surrounding) muscle. For example, the higher the ratio of the signal from nerve tissue vs. signal from muscle tissue, the more the nerve tissue is visually distinguished from surrounding (background) tissue (e.g., in real-time, intraoperatively). The linear peptide does not demonstrate as high ratios. FIGS. 13A-13E also show the signal of the cyclized peptide lasts a longer time compared to the linear peptide, and the ratio of signal from nerve tissue vs. muscle tissue actually increases with time. A longer lasting signal is a benefit because the surgeon has more flexibility in the surgical procedure. For example, administration of the agent does not have to happen immediately before the procedure; rather, there is a longer window of time during which a signal can be detected. The signal is detectable after about 15 minutes, but the nerve/muscle signal ratio actually improves with time. The signal is detectable up to at least a few hours after administration. Similar time periods are expected in humans as in the animal studies.

Figure 14A:
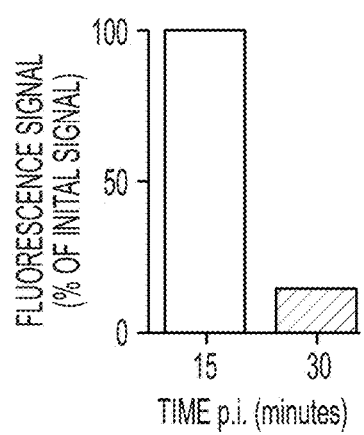
FIGS. 14A and 14B show in vivo imaging of sciatic nerve and muscle fluorescence signal vs time post-injection of 17 AA linear nerve binding peptides.
Figure 14B:
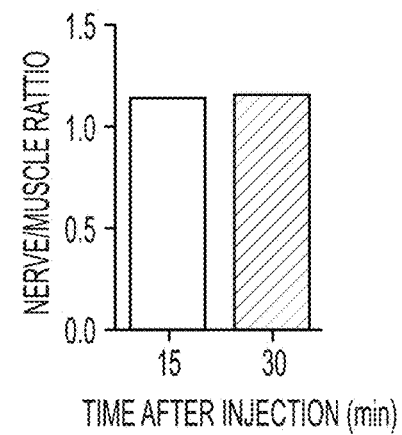

FIGS. 14A and 14B show in vivo time-dependent uptake from sciatic nerve and muscle post-iv injection of 17 AA linear peptide-dye conjugates using optical imaging. 17 AA linear peptide-dye conjugates (Cy5 labeled) were injected intravenously (150 nmole) into the tail veins of nude mouse prior to surgical exposure and imaging of sciatic nerves and adjacent muscle using a Zeiss Lumar stereomicroscope (0.8× objective) with fluorescence imaging capabilities. Pre- and serial post injection (p.i.) images (bright field, fluorescent) were acquired at 6 times points (15 min-150 min) p.i. Bars indicate mean+/−standard deviation. N=5 per group. Each replicate is from one biological experiment, quantified with fiach replicate is from one biological experiment, quantified with is (15 minmind at 6 times and muscle regions to assess time-dependent signal changes. FIG. 14A shows the absolute nerve fluorescence muscle. Fluorescence signal was seen to significantly drop at 30 min to about 15% of the post-injection levels; signal was barely perceptible thereafter, precluding evaluation (data not shown). Moreover, FIG. 14A shows that the signal from linear peptide is reduced to 10% of the initial signal 30 minutes after administration. FIG. 14B shows the corresponding time-varying nerve-to-muscle or contrast ratios, which were roughly equivalent over the first 30 min post-injection of linear peptide-dye conjugate, suggesting selective uptake and retention by the sciatic nerve specimens relative to muscle with time.

Figure 15:
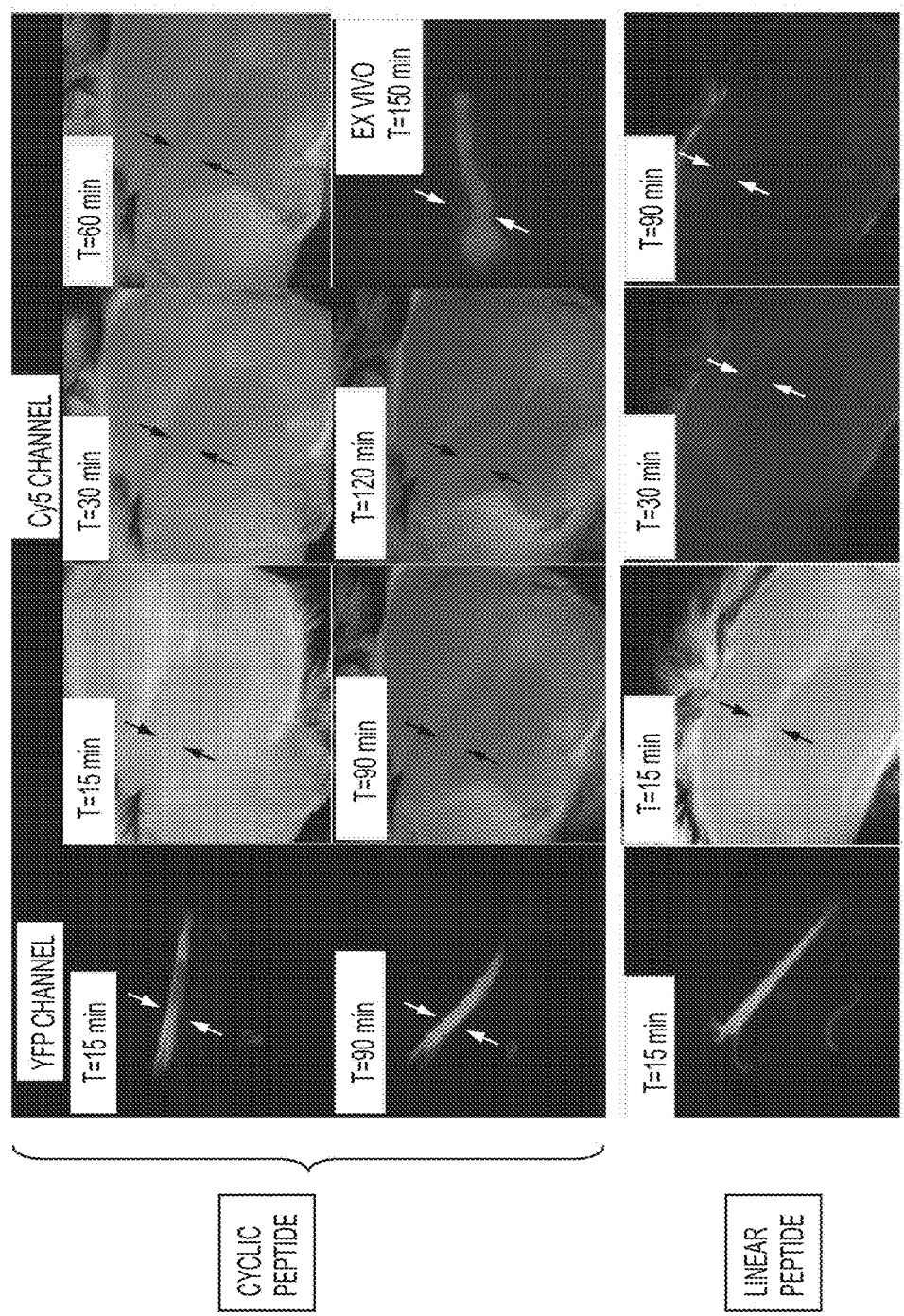
FIG. 15 shows time-dependent in vivo fluorescence microscopy of human sciatic nerve post-injection of 150 nmoles of cyclic vs. linear peptide-dye conjugates in thy1-YFP transgenic mice.

FIG. 15 shows time-dependent in vivo fluorescence microscopy of human sciatic nerve post-injection of 150 nmoles of cyclic vs. linear peptide-dye conjugates in thy1-YFP transgenic mice.

FIGS. 16A-16E show in vivo time-dependent uptake from sciatic nerve and muscle post-iv injection of 17 AA cyclic peptide-dye conjugates using optical imaging. 17 AA cyclic peptide-dye conjugates (Cy5 labeled) were injected intravenously (150 nmole) into the tail veins of nude mouse prior to surgical exposure and imaging of sciatic nerves and adjacent muscle using a Zeiss Lumar stereomicroscope (0.8× objective) with fluorescence imaging capabilities. Pre- and serial post injection (p.i.) images (bright field, fluorescent) were acquired at 6 time points (15 min-150 min) p.i. Bars indicate mean+/−standard deviation. N=5 per group. Each replicate is from one biological experiment, quantified with five independent fields of view. Region of interest (ROI) analysis was performed over nerve and muscle regions to assess time-dependent signal changes. FIGS. 16A-16D show the absolute and relative fluorescence signal (percentage of the initial fluorescence signal acquired at 15 min p.i.) of nerves (FIGS. 16A and 16C) and adjacent muscle (FIGS. 16B and 16D), respectively. FIG. 16E shows time-varying nerve-muscle or contrast ratios, which increased from about 1.3 to nearly 2.6 over a 1.5 hour period. Without wishing to be bound to any theory, these data suggest selective uptake and retention by nerve specimens with time.

What is claimed is:

1. A cyclic nerve-binding peptide conjugate comprising:
  from one to twenty cyclic nerve-binding peptide ligands, each having from 5 to 20 amino acid residues and/or a 15 atom to 60 atom macrocycle, wherein the one to twenty cyclic nerve-binding peptide ligands comprise the peptide sequence NTQTLAKAPEHT (SEQ ID NO: 1);
  a silica-based nanoparticle, wherein the silica-based nanoparticle has a diameter less than 10 nm;
  a fluorescent agent; and
  a linker moiety attached to the silica-based nanoparticle, thereby coating the nanoparticle, wherein the one to twenty cyclic nerve-binding peptide ligands are attached to the coated silica-based nanoparticle.

2. The nerve-binding peptide conjugate of claim 1, wherein the silica-based nanoparticle comprises:
  a silica-based core;
  the fluorescent agent within the core; and
  a silica shell surrounding at least a portion of the core.

3. The nerve-binding peptide conjugate of claim 1, wherein the linker moiety comprises one or more members selected from the group consisting of polyethylene glycol (PEG), $PEG_2$, and para-aminobenzyloxy carbamate (PABC).

4. The nerve-binding peptide conjugate of claim 1, wherein the fluorescent agent comprises a cyanine dye.

5. The nerve-binding peptide conjugate of claim 1, having 17 amino acid residues and/or a 51 atom macrocycle.

6. The nerve-binding peptide conjugate of claim 1, wherein a macrocycle is formed by cyclizing the peptide head-to-tail, or by introducing a covalent bond internal to the sequence.

* * * * *